United States Patent
Naka et al.

(10) Patent No.: US 7,045,602 B2
(45) Date of Patent: May 16, 2006

(54) SPECIFIC ANTIBODY DIRECTED TO ACTIVE HEPATOCYTE GROWTH FACTOR ACTIVATOR AND METHOD FOR USING THE SAME

(75) Inventors: Daiji Naka, Yokohama (JP); Kazuhiko Nagaike, Inashi-gun (JP)

(73) Assignee: Mitsubishi Chemical Corporation, Tokyo (JP)

( * ) Notice: Subject to any disclaimer, the term of this patent is extended or adjusted under 35 U.S.C. 154(b) by 187 days.

(21) Appl. No.: 10/000,096

(22) Filed: Dec. 4, 2001

(65) Prior Publication Data

US 2002/0165362 A1 Nov. 7, 2002

(30) Foreign Application Priority Data

Dec. 5, 2000 (JP) ............................. 2000-370435

(51) Int. Cl.
*C07K 16/00* (2006.01)
*C12P 21/08* (2006.01)
*C12N 1/00* (2006.01)

(52) U.S. Cl. .............................. 530/387.9; 530/388.1; 530/389.1; 530/387.1; 435/810; 435/346

(58) Field of Classification Search ............. 530/387.1, 530/387.9, 388.1, 389.1; 435/810, 346
See application file for complete search history.

(56) References Cited

U.S. PATENT DOCUMENTS

| 4,281,061 A | * | 7/1981 | Zuk et al. ..................... 435/7.9 |
| 5,466,593 A | | 11/1995 | Shimomura et al. ......... 435/219 |
| 5,677,164 A | | 10/1997 | Shimomura et al. ......... 435/226 |

FOREIGN PATENT DOCUMENTS

| EP | 0596524 | 5/1994 |
| JP | 5103670 | 4/1993 |
| JP | 6-153946 | 6/1994 |
| JP | 6-153966 | 6/1994 |

OTHER PUBLICATIONS

Goldsby et al Immunology, Fifth edition, 2000, pp. 137-139).*
K. Miyazawa et al., "Molecular Cloning and Sequence Analysis of the cDNA for a Human Serine Protease Responsible for Activation of Hepatocyte Growth Factor", The Journal of Biological Chemistry, vol. 268, No. 14, pp. 10024-10028 (1993).
T. Shimomura et al., "A novel protease obtained from FBS-containing culture supernatant, that processes single chain form hepatocyte growth factor to two chain form in serum-free culture", Cytotechnology 8:219-229 (1992).
K. Miyazawa et al., "Activation of Hepatocyte Growth Factor in the Injured Tissues is Mediated by Hepatocyte Growth Factor Activator", The Journal of Biological Chemistry, vol. 271, No. 7, pp. 3615-3618 (1996).
T. Shimomura et al., "Activation of the Zymogen of Hepatocyte Growth Factor Activator by Thrombin", The Journal of Biological Chemistry, vol. 268, No. 30, pp. 22927-22932. (1993).
T. Shimomuru et al., "Identification and Analysis of the Hepatocyte Growth Factor Activator from Human Blood", Mitsubishi Kasei R&D Review, 1994, vol. 8, No.: 1 pp. 26-35.
T. Shimomura et al., "Activation of the Zymogen of Hepatocyte Growth Factor Activator by Thrombin". Journal of Biological Chemistry, American Society of Biological Chemists, Oct. 1993, XP000197750.
Patent Abstracts of Japan vol. 018, No. 420, Aug. 1994 & JP 06130066A, May 1994 Abstract.
T. Shimomura et al., "Activation of Hepatocyte Growth Factor by Two Homologous Proteases Blood-Coagulation Factors XIIa and Hepatocyte Growth Factor Activator", European Journal of Biochemistry, Apr. 1995, XP001062759.
H. Kataoka et al., "Activation of Hepatocyte Growth Factor/Scatter Factor in Colorectal Carcinoma", Cancer Research, 2000, vol. 60, pp. 6148-6159.

* cited by examiner

*Primary Examiner*—Christina Chan
*Assistant Examiner*—Michail Belyavskyi
(74) *Attorney, Agent, or Firm*—Wenderoth, Lind & Ponack, L.L.P.

(57) ABSTRACT

An antibody which recognizes an active hepatocyte growth factor activator (HGFA) and does not substantially recognize inactive HGFA is provided. Also disclosed is a monoclonal antibody thereof, and a hybridoma cell line for producing the monoclonal antibody. There is further provided a method for measuring active HGFA using the antibody, and a method for detecting a disease, by detecting or measuring active HGFA using the antibody.

18 Claims, 5 Drawing Sheets

SEQUENCE LISTING

<160> NUMBER OF SEQ ID NOS: 3

<210> SEQ ID NO 1
<211> LENGTH: 13
<212> TYPE: PRT
<213> ORGANISM: Homo sapiens

<400> SEQUENCE: 1

Gly Arg Arg His Lys Lys Arg Thr Phe Leu Arg Pro Arg
 1               5                  10

<210> SEQ ID NO 2
<211> LENGTH: 13
<212> TYPE: PRT
<213> ORGANISM: Homo sapiens

<400> SEQUENCE: 2

Ile Ile Gly Gly Ser Ser Ser Leu Pro Gly Ser His Pro
 1               5                  10

<210> SEQ ID NO 3
<211> LENGTH: 26
<212> TYPE: PRT
<213> ORGANISM: Homo sapiens

<400> SEQUENCE: 3

-continued

```
Gly Arg Arg His Lys Lys Arg Thr Phe Leu Arg Pro Arg Ile Ile Gly
 1               5                  10                  15

Gly Ser Ser Ser Leu Pro Gly Ser His Pro
            20              25
```

US 7,045,602 B2

SPECIFIC ANTIBODY DIRECTED TO ACTIVE HEPATOCYTE GROWTH FACTOR ACTIVATOR AND METHOD FOR USING THE SAME

BACKGROUND OF THE INVENTION

1. Field of the Invention

The present invention relates to an antibody or a monoclonal antibody used for specifically measuring active hepatocyte growth factor activator (HGFA), a method for using the same and a measurement kit. The present invention also relates to a method for detecting a disease of patient in a pathological condition, in particular, organ inflammation, glomerular nephritis, cancer, myocardial infarction, angina pectoris or thrombosis, by using the active HGFA as an index and further relates to a method for collecting a biological component and blood, which is suitable for performing the method.

2. Description of the Related Art

Protease (protein decomposition enzyme) is a protein having a function of hydrolyzing a peptide bond in a protein or a peptide and it is deeply involved in organic functions and, at the same time, plays an important role in maintenance of homeostasis thereof. For example, various proteases existing in blood themselves constitute dense cascades and control coagulation and fibrinolysis of blood.

A hepatocyte growth factor activator (hereinafter abbreviated as "HGFA") is known as a kind of serine protease having a serine residue in its active center (Miyazawa et al., *J. Biol. Chem.*, 268, pp.10024–10028, 1993). Unlike common proteases in blood involved in the blood coagulation/fibrinolysis system cascades, HGFA has a unique characteristic of acting on a hepatocyte growth factor (hereinafter abbreviated as "HGF"), which is known as a cytokine involved in hepatocyte growth or organ regeneration (Naka et al., *J. Biol. Chem.*, 267, pp.20114–20119, 1992), to specifically and limitedly decompose it and thereby activate it (Shimomura et al., *Cytotechnology*, 8, pp.219–229 (1992)). However, as for the action of HGFA, only the activation of HGF is known in animal model experiments using rats or in vitro experiments (Miyazawa et al., *J. Biol. Chem.*, 271, pp.3615–3618, 1996), and its roles and functions in human pathologic conditions and the relationship of its blood level and pathologic conditions have not been known at all.

As HGFA, there are known one showing a molecular weight of about 96,000–98,000 determined by SDS-PAGE (hereafter, abbreviated as "98 kDa HGFA") and one showing a molecular weight of about 34,000–38,000 (hereafter, abbreviated as "36 kDa HGFA"), which is a peptide on the C terminus side of the protein provided by limited proteolysis at a bond between arginine at a position of 372 and the valine at a position of 373, which are counted from the translation initiation amino acid. The variation in the molecular weights is caused by heterogeneity in the bonding amount of sugar chains and differences in measured molecular weight values attributable to whether the measurement by the SDS-PAGE method was performed under reducing or non-reducing condition, and these are essentially the same protein. Further, each HGFA usually exists as an inactive substance in blood, but is activated by limited proteolysis at a bond between the arginine at position of 407 and isoleucine at a position of 408, which are counted from the translation initiation amino acid, and thus single chain HGFA is converted to double chain HGFA, which is heterodimerized with a disulfide bond. This activated HGFA is considered to specifically activate the substrate, HGF (Shimomura et al., *J. Biol. Chem.*, 268, pp.22927–22932, 1993).

To analyze the relationship between the HGFA blood level and pathological conditions, active HGFA existing in biological component such as human tissues, humors or blood needs to be specifically measured. Further, to specifically detect or measure active HGFA, it is essential to obtain an antibody, particularly preferably a monoclonal antibody, that recognizes active HGFA extremely specifically, but does not substantially recognize inactive HGFA. However, any antibody having such a characteristic has not known at all so far. Further, there is no method or kit specifically used for measuring active HGFA existing in a biological component such as human blood.

SUMMARY OF THE INVENTION

Accordingly, an object of the present invention is to provide an antibody that specifically recognizes active HGFA and does not substantially recognize inactive HGFA, a method for measuring active HGFA by using the antibody and a method and kit for detecting a disease associated with active HGFA.

The inventors of the present invention constructed a system for quantifying HGFA in human blood to analyze the relationship between the HGFA blood level and various human diseases as for human pathological conditions. First, they constructed an enzyme-labeled antibody measurement system using the double antibody sandwich method (enzyme-linked immunosorbent assay, abbreviated as "ELISA measurement system" hereafter) by using 7E10, P1–4, A-1, A-6, A-23, A-32, A-51, A-75, which are known as existing mouse monoclonal antibodies directed to HGFA (Miyazawa et al., *J. Biol. Chem.*, 271, pp.3615–3618, 1996). Further, they analyzed reactivity of HGFA monoclonal antibodies in blood (plasma or serum) of healthy subjects and patients with various diseases including organ diseases. However, uniformly strong reactivity was observed in all human blood including that of normal subjects by the ELISA measurement system using these monoclonal antibodies, and no reactivity specific to human diseases, that is, no marked changes in the HGFA blood level could be detected. Therefore, the inventors of the present invention analyzed reactivity to HGFA of the existing monoclonal antibodies directed to HGFA to investigate causes therefor.

First, since there are two forms of HGFA, active and inactive types, reactivity to HGFA of monoclonal antibodies directed to respective HGFA was analyzed. More specifically, active HGFA and inactive HGFA were adhered to a solid phase plate, and reactivity between the HGFA adhered to the solid phase and respective monoclonal antibodies was analyzed. As a result, it was found that these monoclonal antibodies had a characteristic of being reactive to both of active HGFA and inactive HGFA. These results suggested that, in the ELISA method using existing monoclonal antibodies, inactive HGFA, which is considered to constantly exist in blood in a large amount (Shimomura et al., *J. Biol. Chem.*, 268, pp.22927–22932, 1993), is measured, or both of a trace amount of active HGFA and inactive HGFA are measured. Thus, it was found that the ELISA measurement system using existing monoclonal antibodies could not reveal the relationship between HGFA and human diseases at all.

Then, paying attention to the fact that HGFA exists in two forms, active and inactive types, the inventors of the present invention specifically detected an activated state of HGFA existing in a human living bodies and examined the relationship between various human diseases and the amount of active HGFA in blood of patients with those diseases. As a result of their assiduous studies, they successfully produced polyclonal antibodies and monoclonal antibodies that recognize active HGFA but do not substantially recognize inactive HGFA for the first time. Further, they accomplished a method and kit that react with active HGFA existing in a human biological component but do not substantially react with inactive HGFA, that is, a method and kit for specifically measuring active HGFA, by utilizing an immunoassay using the antibodies.

Further, the inventors found for the first time that, when the method and kit for specifically measuring active HGFA of the present invention are used, there could be observed a markedly increased amount of active HGFA in blood of patients with organ derangement including glomerular nephritis and cancer patients compared with that of healthy subjects. Further, they also found for the first time that thrombosis such as angina pectoris, myocardial infarction and cerebral infarction could be accurately predicted by using the increase in the amount of active HGFA in blood as an index.

Meanwhile, when the amount of active HGFA existing in a biological component including human blood is measured, there is required a method of stably collecting active HGFA existing therein with good reproducibility. The inventors of the present invention examined addition of various protease inhibitors and so forth in this method and found that active HGFA could be extremely stably measured with good reproducibility by adding argatroban, which is a selective thrombin inhibitor. Further, as a result of many detailed investigations, they also found that argatroban was effective even when human blood such as whole blood, serum or plasma was collected and that an extremely favorable result could be obtained by using citrated plasma among blood components.

The present invention was accomplished based on the above findings and provides the followings.

(1) An antibody that recognizes an active hepatocyte growth factor activator (HGFA) and does not substantially recognize inactive HGFA.
(2) The antibody according to (1), which shows a dissociation constant of $1\times10^{-8}$ M or lower for active HFGA.
(3) The antibody according to (1) or (2), which is a monoclonal antibody.
(4) The antibody according to (3), which recognizes active HGFA showing a molecular weight of about 34,000–98,000 determined by the SDS-PAGE method and does not substantially recognize inactive HGFA.
(5) The antibody according to (4), which recognizes active HGFA showing a molecular weight of about 34,000–38,000 determined by the SDS-PAGE method.
(6) The monoclonal antibody according to (4), which is produced by a hybridoma of an accession number FERM BP-7779.
(7) A monoclonal antibody that recognizes active HGFA activated by limited proteolysis of inactive HGFA, which is a precursor of active HGFA, between arginine at a position of 407 and isoleucine at a position of 408 counted from a translation initiation amino acid of inactive HGFA, and does not substantially recognize inactive HGFA
(8) A monoclonal antibody that recognizes active HGFA and does not substantially recognize inactive HGFA and a complex of active HGFA and a protease inhibitor.
(9) A hybridoma cell line that produces a monoclonal antibody according to any one of (3) to (8).
(10) A method for measuring active HGFA, comprising the step of measuring the active HGFA specifically by an immunological method using one or more kinds of antibodies according to any one of (1) to (8).
(11) The method according to (10), wherein a specimen to be measured for active HGFA is a biological component collected from a subject or test animal suspected of having a disease.
(12) The method according to (11), wherein the disease is organ inflammation, glomerular nephritis, cancer, myocardial infarction, angina pectoris, cerebral infarction or thrombosis.
(13) A method for detecting a disease, comprising the step of detecting or measuring active HGFA in a biological component collected from a subject suspected of having a disease.
(14) The method according to (13), wherein the disease is selected from the group consisting of organ inflammation, glomerular nephritis, cancer, myocardial infarction, angina pectoris, cerebral infarction and thrombosis.
(15) The method according to (13) or (14), wherein the biological component is blood or a fraction or processed product thereof.
(16) The method according to (15), wherein the biological component is plasma.
(17) The method according to (16), wherein the plasma is citrated plasma.
(18) The method according to any one of (13) to (17), wherein argatroban is added to the biological component.
(19) A kit for detecting or measuring active HGFA, which comprises one or more kinds of antibodies according to any one of (1) to (8).
(20) The kit according to (19), which is used for diagnosis of disease selected from the group consisting of organ inflammation, glomerular nephritis, cancer, myocardial infarction, angina pectoris, cerebral infarction and thrombosis.
(21) The kit according to (19) or (20), which is used to measure active HGFA in a biological component collected from a subject suspected of having a disease.
(22) The kit according to any one of (19) to (21), wherein active HFGA is detected or measured by immunostaining.
(23) A blood collection tube for collecting serum, plasma or whole blood, which is added with argatroban.
(24) The blood collection tube according to (23), which is used to collect serum, plasma or whole blood to be used for measurement of active HGFA.

In the present specification, a monoclonal antibody that recognizes active HGFA and does not substantially recognize inactive HGFA may be referred to as "active HGFA specific monoclonal antibody", and a polyclonal antibody that recognizes active HGFA and does not substantially recognize inactive HGFA may be referred to as "active HGFA specific polyclonal antibody". Further, these antibodies may be collectively referred to as "active HGFA specific antibody". Further, "recognizing active HGFA" means bonding to active HGFA through an antigen/antibody reaction and preferably means that a dissociation constant for active HGFA is $1\times10^{-8}$ M or lower, more preferably $1\times10^{-9}$ M or lower.

"Not substantially recognizing inactive HGFA" means not substantially bonding to inactive HGFA through an antigen/antibody reaction. More specifically, "not substantially recognizing inactive HGFA" means that inactive HGFA cannot be detected by a usual immunoassay and that a dissociation constant for inactive HGFA is $1\times10^{-5}$ M or higher.

According to the present invention, there are provided monoclonal and polyclonal antibodies that specifically bond to active HGFA and do not bond to inactive HGFA. The antibodies of the present invention can be used for specific measurement and detection of active HGFA.

The method for specifically measuring active HGFA of the present invention can be used for diagnosis of various diseases reflected in blood level of active HGFA.

BRIEF DESCRIPTION OF THE DRAWINGS

FIG. 3 shows reactivities between active HGFA and inactive HGFA and monoclonal antibody measured by an active HGFA measurement system.

DETAILED DESCRIPTION OF THE INVENTION

Figure 1:
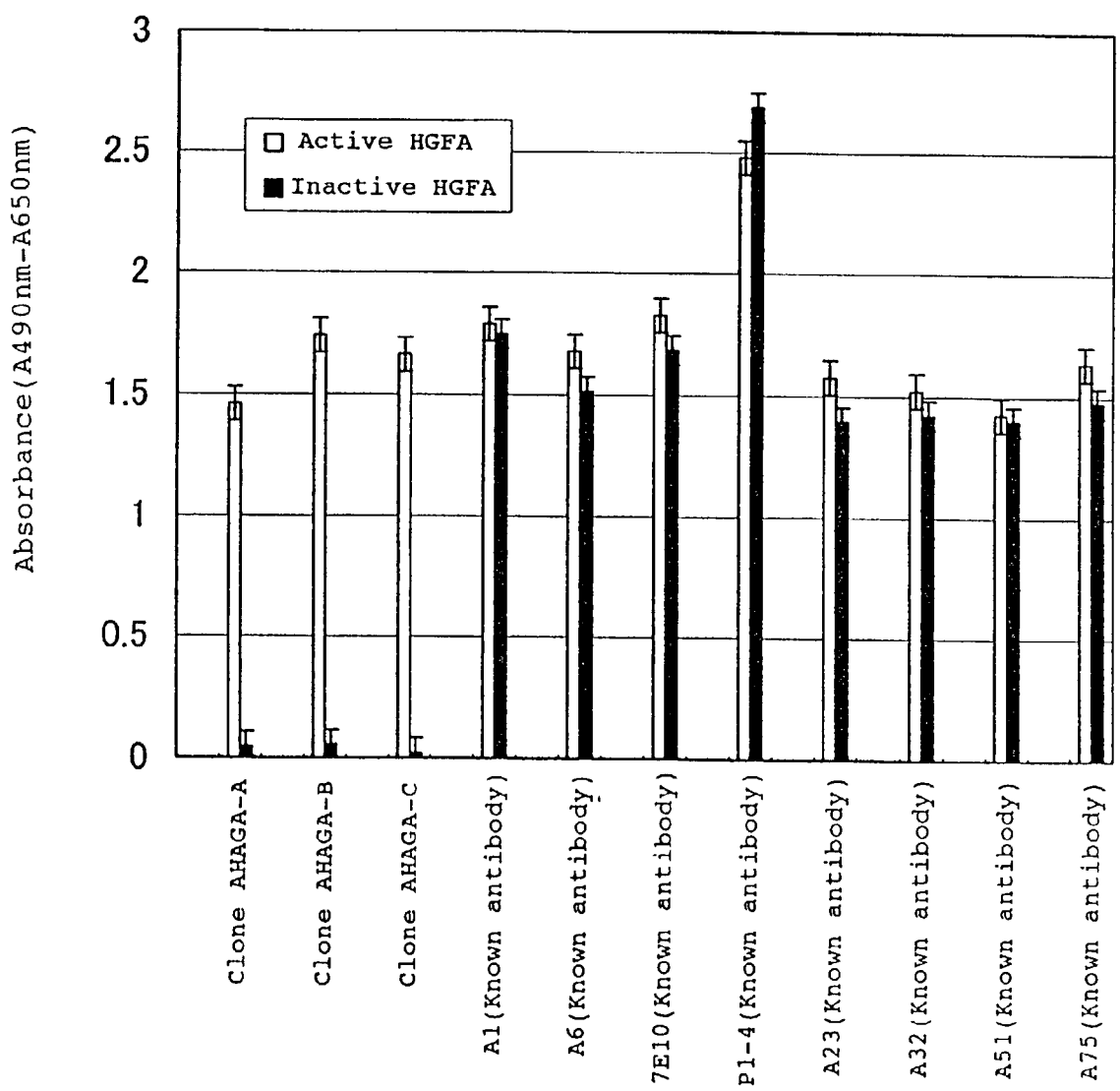
FIG. 1 shows reactivities of monoclonal antibody to active HGFA and inactive HGFA.

The present invention will be explained in detail hereafter.

<1> Immunogen and Screening Antigen for Production of Specific Antibody Directed to Active HGFA The term "active HGFA" used in the present invention refers to a substance having an ability to act on its substrate, hepatocyte growth factor (HGF), to convert its inactive type, single chain HGF (Naka et al., *J. Biol. Chem.*, 267:20114–20119 (1992)), into its active type, double chain HGF. The single chain HGF refers to a protein obtained from a precursor protein translated from the HGF gene by removal of the signal peptide, and the double chain HGF refers to a heterodimer consisting of two chains formed by limited proteolysis of HGF between arginine at a position of 494 and valine at a position of 495 counted from the translation initiation amino acid and heterodimerized with a disulfide bond. The activity of HGFA refers to an activity of converting inactive single chain HGF into active double chain HGF.

Active HGFA includes, specifically, HGFA obtained by activation of the HGFA precursor protein disclosed in Japanese Patent Laid-open Publication (Kokai) No. 6-153946 through limited proteolysis between arginine at a position of 407 and isoleucine at a position of 408, which are counted from the translation initiation amino acid. This active HGFA normally shows a molecular weight of about 34,000–98,000 determined by the SDS-PAGE method, and there are known active HGFAs obtained by limited proteolysis of the N-terminus portion and showing various molecular weights (Mitsubishi Kasei R & D Review, 8 (1), 26–35 (1994)). As examples of such HGFAs, there are one showing a molecular weight of about 98,000 as determined by SDS-PAGE under a reducing condition, one corresponding to a C-terminus side peptide of the same obtained by limited proteolysis between arginine at a position of 88 and the alanine at a position of 89, which are counted from the translation initiation amino acid, and showing a molecular weight of about 80,000, and one corresponding to a C-terminus side peptide obtained by limited proteolysis of the same between the arginine at a position of 372 and valine at a position of 373, which are counted from the translation initiation amino acid, and showing a molecular weight of about 36,000. The aforementioned one showing a molecular weight of about 98,000 may show a molecular weight in the range of about 96,000 to 98,000, and the aforementioned one showing a molecular weight of about 36,000 may show a molecular weight in the range of about 34,000 to 38,000, depending on heterogeneity of the amount of bonded sugar chains, method of molecular weight measurement or purification method. Therefore, active HGFA referred to herein is not limited by its molecular weight, and includes those having the ability to activate its substrate, HGF.

As active HGFA or inactive HGFA used as immunogen, used for screening of monoclonal antibody and so forth, there may be used those purified from blood of human according to the method of Shimomura et al. (*J. Biol. Chem.*, 268:22927–22932 (1993)) and so forth. Further, it is also possible to use HGFA that is a recombinant protein obtained by using HGFA cDNA disclosed in Japanese Patent Laid-open Publication Nos. 6-153966 and 6-153946, U.S. Pat. No. 5,466,593 and U.S. Pat. No. 5,677,164 and a microorganism such as *Escherichia coli*, an insect cell, yeast, an animal cell or an animal.

In order to obtain an active HGFA specific antibody, in particular, it is required to prepare active HGFA of high purity not containing inactive HGFA and inactive HGFA of high purity not containing active HGFA as an antigen for immunization or an antigen for screening. For these purposes, recombinant proteins obtained by using HGFA cDNA are preferred as active HGFA and inactive HGFA used in the present invention. For example, recombinant protein HGFA can be obtained by inserting a full length or a part of HGFA cDNA coding for the HGFA precursor disclosed in Japanese Patent Laid-open Publication No. 6-153946 into a suitable vector, introducing the vector into a microorganism such as *Escherichia coli*, an insect cell, yeast, an animal cell or an animal and performing purification operation for culture supernatant of the transgenic cells, intracellular content, tissue or body fluid.

It is also possible to produce a target HGFA, without using a cell system, by using an in vitro transcription and translation system utilizing Rapid Translation System RTS500 (Roshe Diagnostics) or the like.

Specifically, there can be used a method utilizing an expression vector obtained by inserting HGFA cDNA coding for 655 amino acids that correspond to the full length of inactive HGFA precursor including the signal sequence disclosed in Japanese Patent Laid-open Publication No. 6-153946 into an animal cell expression vector downstream from a promoter, a method utilizing an animal cell expression vector obtained by ligating a suitable signal sequence and cDNA coding for the C-terminus side portion of the HGFA precursor from valine at a position of 373, which is counted from the translation initiation amino acid, as disclosed in Japanese Patent Laid-open Publication 6-153966, and a method utilizing an animal cell expression vector obtained by ligating a suitable signal sequence and cDNA coding for a region having an ability to exert the HGFA activity. HGFA that is a recombinant protein can be obtained by introducing any of these expression vectors into an animal cell, then selecting a cell expressing the HGFA cDNA, and purifying HGFA of interest from culture supernatant of the cell.

HGFA that is a recombinant protein obtained by such a method is generally inactive HGFA. This inactive HGFA can be activated by adding suitable amounts of thrombin and dextran sulfate or kallikrein and thrombin to the inactive HGFA referring to the method of Shimomura et al. (*J. Biol. Chem.*, 268:22927–22932 (1993)). Purity of HGFA activated by this treatment can be increased through purification by gel filtration or affinity chromatography utilizing HPLC.

Not only purified active HGFA and inactive HGFA of high purity are important as immunogens, but also they can serve as extremely important materials in case of selection of active HGFA specific polyclonal antibodies by affinity purification or screening of active HGFA specific monoclonal antibodies.

As a result of detailed study of the inventors of the present invention, it was found that purified inactive HGFA was extremely unstable and it might be activated by contamination of a small amount of impurities. If such inactive HGFA contaminated with active HGFA is used, or conversely, if active HGFA contaminated with inactive HGFA is used, it would be difficult to obtain an active HGFA specific polyclonal antibody or an active HGFA specific monoclonal antibody. Then, the inventors of the present invention investigated various protease inhibitors as an inhibitor for preventing the artificial activation at the time of preparing inactive HGFA. As a result, they found that it was effective to add argatroban (Mitsubishi-Tokyo Pharmaceuticals), which is a selective thrombin inhibitor, to HGFA. That is, if argatroban is added to inactive HGFA upon purification of the inactive HGFA or screening of monoclonal antibodies, it is possible to prevent the artificial activation thereof and contamination with active HGFA. Active HGFA prepared in such a manner is suitable as an antigen for immunization for obtaining an active HGFA specific antibody, and it can also be used as a material for selecting and purifying an antibody that recognizes active HGFA but does not substantially recognize inactive HGFA.

On the other hand, inactive HGFA is suitable as an antigen for immunization for obtaining an antibody that recognizes inactive HGFA but does not substantially recognize active HGFA, and it can be used as a material for selecting, absorbing or removing antibodies other than the antibody that recognizes active HGFA and does not substantially recognize inactive HGFA.

It is possible to use a peptide located at a site showing difference of primary structure sequence (amino acid sequence) or difference of conformation between active HGFA and inactive HGFA as an antigen for immunization required for obtaining an active HGFA specific antibody or an antigen for screening. For example, it is possible to use a peptide at a site that is exposed only on the protein surface of active HGFA, but is not exposed on the protein surface of inactive HGFA. Such conformation of proteins can generally be predicted by those skilled in the art, and three-dimensional conformational structures diagrammed by using a computer program based on the amino acid sequences of active HGFA and inactive HGFA are available. By comparison of the both conformations, it is possible to find out a region that serves as a binding site for an antibody showing specific reactivity to active HGFA (antigenic site) and use a peptide obtained by synthesizing a partial amino acid sequence of that region as an immunogen.

Further, it is also possible to find out a region that serves as a site showing a difference between active HGFA and inactive HGFA for hydrophilicity or hydrophobicity, difference in results of secondary structure analysis based on the Cho-Fasman method, the Robson method or the like or difference in antigenicity based on the information of the amino acid sequence of HGFA by using protein structure analysis software such as GENETYX (SOFTWARE DEVELOPMENT CO., LTD), and use a peptide obtained by synthesizing a partial amino acid sequence of that region as an immunogen or screening antigen. For example, active HGFA has an amino acid sequence obtained by limited proteolysis of the HGFA precursor protein between arginine at a position of the 407 and isoleucine at a position of 408, which are counted from the translation initiation amino acid. On the other hand, inactive HGFA has an amino acid sequence in which these 407th arginine and 408th isoleucine are connected. Therefore, as an amino acid sequence that does not exist in inactive HGFA but exists only in inactive HGFA, a peptide containing the 407th arginine as the C-terminus and a sequence of several amino acids existing on its N-terminus side can be utilized. As example of such a peptide, the followings can be selected. The amino acid sequences of Sequences 2 to 12 correspond to sequences formed by deleting amino acid residues from the amino acid sequence of Sequence 1 (SEQ ID NO: 1) one by one from the N-terminus side.

| Sequence 1:  | GRRHKKRTFLRPR | (SEQ. ID. NO.:1)  |
|---|---|---|
| Sequence 2:  | RRHKKRTFLRPR  | (SEQ. ID. NO.:4)  |
| Sequence 3:  | RHKKRTFLRPR   | (SEQ. ID. NO.:5)  |
| Sequence 4:  | HKKRTFLRPR    | (SEQ. ID. NO.:6)  |
| Sequence 5:  | KKRTFLRPR     | (SEQ. ID. NO.:7)  |
| Sequence 6:  | KRTFLRPR      | (SEQ. ID. NO.:8)  |
| Sequence 7:  | RTFLRPR       | (SEQ. ID. NO.:9)  |
| Sequence 8:  | TFLRPR        | (SEQ. ID. NO.:10) |
| Sequence 9:  | FLRPR         | (SEQ. ID. NO.:11) |
| Sequence 10: | LRPR          | (SEQ. ID. NO.:12) |
| Sequence 11: | RPR           |                   |
| Sequence 12: | PR            |                   |

Further, as an amino acid sequence that does not exist in inactive HGFA but exists only in active HGFA, a peptide containing the isoleucine at a position of 408 as the N-terminus and a sequence of several amino acids existing on its C-terminus side, the followings can be selected. The amino acid sequences of Sequences 14 to 24 correspond to sequences formed by deleting amino acid residues from the amino acid sequence of Sequence 13 (SEQ ID NO: 2) one by one from the C-terminus side.

| Sequence 13: | IIGGSSSLPGSHP | (SEQ. ID. NO.:2)  |
|---|---|---|
| Sequence 14: | IIGGSSSLPGSH  | (SEQ. ID. NO.:13) |
| Sequence 15: | IIGGSSSLPGS   | (SEQ. ID. NO.:14) |
| Sequence 16: | IIGGSSSLPG    | (SEQ. ID. NO.:15) |
| Sequence 17: | IIGGSSSLP     | (SEQ. ID. NO.:16) |
| Sequence 18: | IIGGSSSL      | (SEQ. ID. NO.:17) |
| Sequence 19: | IIGGSSS       | (SEQ. ID. NO.:18) |
| Sequence 20: | IIGGSS        | (SEQ. ID. NO.:19) |

-continued

Sequence 21: IIGGS (SEQ. ID. NO.:20)

Sequence 22: IIGG (SEQ. ID. NO.:21)

Sequence 23: IIG

Sequence 24: II

Further, as an amino acid sequence that does not exist in active HGFA but exists only in inactive HGFA, a peptide containing an amino acid sequence in which the arginine at a position of 407 and isoleucine at a position of 408 (between the positions of 13 and 14 of Sequence 25) of the HGFA precursor, which are counted from the translation initiation amino acid, are connected, such as Sequence 25 (SEQ ID NO: 3), can be selected.

Sequence 25: GRRHKKRTFLRPRIIGGSSSLPGSHP (SEQ. ID. NO.:3)

When these peptides are used as antigens for immunization, it is generally desirable to use those peptide bound to a protein or polymer such as KLH (keyhole limpet hemocyanin), BSA (bovine serum albumin) and OVA (ovalbumin) as a carrier as an antigen for immunization. For example, those consisting one of the peptides of Sequences 1 to 12 added with cysteine at the N-terminus, those consisting one of the peptides of Sequences 13 to 24 added with cysteine at the C-terminus, and those consisting the peptide of Sequence 25 added with cysteine at the N-terminus or C-terminus can be synthesized, bound to Imject Maleimide Activated Carrier Proteins (PIERCE), and use as antigens for immunization.

Moreover, it is also possible to use a fusion protein obtained by ligating cDNA corresponding any one of Sequences 1 to 25 and cDNA for a protein that serves as the carrier, expressing a fusion protein consisting of the peptides encoded by the both from it in various cells using genetic engineering techniques, and purifying the fusion protein. A peptide containing any one of Sequences 1 to 24 is suitable as an antigen for immunization for obtaining an active HGFA specific antibody, and can also be used as a material for selecting and purifying an active HGFA specific antibody. On the other hand, a peptide like Sequence 25 is suitable as an antigen for immunization for obtaining an antibody that recognizes inactive HGFA but does not substantially recognize active HGFA, and can be used as a material for absorbing or removing antibodies other than active HGFA specific antibody.

<2> Production of Monoclonal Antibody Recognizing Active HGFA and not Substantially Recognizing Inactive HGFA In order to obtain an active HGFA specific monoclonal antibody, a usually performed immunological method can be carried out by using the aforementioned active HGFA as an antigen for immunization. For example, active 98 kDa HGFA, active 36 kDa HGFA, or a mixture of the both can be used.

Further, a peptide containing any one of Sequences 1 to 24 is fused to a carrier by the method described above and one or more kinds of such a substance can be mixed and used as an antigen for immunization. Furthermore, it is also possible to use a peptide containing a specific antigenic site for active HGFA.

The animal used for immunization is not particularly limited, and any of rabbit, goat, sheep, mouse, rat, guinea pig, fowl and so forth can be used. The antigen for immunization is sufficiently mixed with complete Freund's adjuvant, incomplete Freund's adjuvant or the like, and then inoculated to an animal subcutaneously, intramuscularly or intraperitoneally. The inoculation is performed every 2 weeks to 5 weeks and continued until antibody titer of the immunized animal with respect to the inoculated antigen sufficiently rises. Then, only the antigen is administered to the immunized animal by intravenous injection, after 3 days, spleen or lymph node considered to contain antibody-producing cells are collected, and the spleen cell or lymph cell is fused to a tumor cell. Then, an antibody-producing cell immortalized by the cell fusion (hybridoma) is isolated. While it is desirable that the tumor cell used herein should be derived from the same species as the immunized animal from which the spleen cell or lymph cell is prepared, it may be heterozoic tumor cell.

As examples of the tumor cell, myeloma cells such as p3 (p3/×63-Ag8), P3U1, NS-1, MPC-11, SP 2/0, FO, ×63.6.5.3, S194 and R210 are used. The cell fusion can be performed by a method generally performed, and it can be performed according to, for example, the description of "Monoclonal Antibody Experimental Manual" (Kodansha Scientific, 1987). The cell fusion can be performed by adding a cell fusion promoting agent to a fusion medium in which cells to be fused are suspended. Examples of the cell fusion promoting agent include Sendai virus, polyethylene glycol having an average molecular weight of 1000–6000 and so forth. In this case, in order to further enhance fusion efficiency, auxiliary materials such as dimethyl sulfoxide, cytokines such as IL-6 and so forth can also be added to the fusion medium. As for the mixing ratio of the tumor cells to the immunized spleen cells or lymph cells, for example, the spleen cells or lymph cell can be used in an approximately equivalent amount to 10-fold amount with respect to the tumor cells.

As the aforementioned fusion medium, various usual media such as ERDF medium, RPMI-1640 medium and MEM medium can be used, and it is usually desirable to eliminate blood serum such as fetal bovine serum (FBS) from the medium during the fusion. The fusion is performed by sufficiently mixing predetermined amounts of the spleen cells or lymph cells subjected to the aforementioned immunization and the tumor cells in the aforementioned medium, adding a polyethylene glycol solution warmed to about 37° C. beforehand in an amount of from about 20% to 50%, and allowing them to react preferably at 30° C. to 37° C. for about 1 minute to 10 minutes. Thereafter, there are repeated operations of occasionally adding a suitable medium, centrifuging the medium and removing the supernatant.

A target hybridoma is cultured in a usual selective medium, for example, HAT medium (medium containing hypoxanthine, aminopterin and thymidine). The culture in this HAT medium may be performed for a period sufficient for cells other than the hybridoma (not fused cells etc.) to be killed, usually several days to several weeks. As for acquisition of an active HGFA specific monoclonal antibody, the most technically important point is the screening thereof. The screening of a hybridoma producing active HGFA specific monoclonal antibody is enabled by using the aforementioned materials such as active HGFA and inactive HGFA and performing analyses thorough various immunochemical methods. For example, a target hybridoma can be selected by using active HGFA or inactive HGFA as an antigen for screening and analyzing the binding of the antigen for screening with a monoclonal antibody secreted in the culture supernatant of the hybridoma based on an enzyme immunoassay such as ELISA, Western blotting or the like.

Specifically, active HGFA is adhered to a screening plate or the like, blocked with BSA or the like, and added with the aforementioned culture supernatant of hybridoma to select hybridomas secreting antibodies that recognize active HGFA. The selected hybridomas were added to inactive HGFA adhered to a screening plate or the like and blocked with BSA or the like to further select hybridomas secreting antibodies that do not recognize this inactive HGFA. For example, the culture supernatant of hybridoma subjected to selection is added to a plate for ELISA adhered with active HGFA or inactive HGFA and allowed to react, and after sufficient washing operation, the plate was added with labeled anti-mouse IgG polyclonal antibodies to further perform a reaction. After washing operation, the label is detected to select a hybridoma that provides a culture supernatant that shows reactivity to the plate adhered with active HGFA, but showing no reactivity to the plate adhered with inactive HGFA. As the label, there are used various enzymes, fluorescent substances, chemiluminescent substances, radioactive isotopes, biotin, avidin and so forth, which will be described later.

By the above screening, there can be obtained a hybridoma that producing a monoclonal antibody that recognizes active HGFA but does not substantially recognize inactive HGFA. Further, in the screening of such a hybridoma, an event that an antibody reacts with a peptide containing any one of the aforementioned Sequences 1 to 24 but does not react with a peptide containing Sequence 25 or the like can be used as an index. As for an antibody produced by a hybridoma selected in such a manner, it is preferable to further confirm that the antibody reacts with active HGFA but does not react with inactive HGFA.

The reactivity of the aforementioned antibody can be confirmed by measuring the dissociation constant for active HGFA or inactive HGFA. The dissociation constant of the antibody of the present invention with respect to active HGFA is preferably $1 \times 10^{-8}$ M or less, more preferably $1 \times 10^{-9}$ M or less. The dissociation constant with respect to inactive HGFA is preferably $1 \times 10^{-5}$ M or more.

The obtained hybridoma can be cloned by the limiting dilution method to obtain a hybridoma clone producing a single kind of monoclonal antibody. This hybridoma clone is cultured in a medium supplemented with about 1 to 5% FBS from which bovine antibodies (IgG) contained in the FBS are eliminated beforehand or a medium for serum free culture, and the obtained culture supernatant is used as a raw material for purification of the target monoclonal antibody. Further, it is also possible to transfer the obtained hybridoma clone into abdominal cavity of Balb/C mouse or Balb/c (nu/nu) mouse administered with pristane beforehand and extract ascites containing monoclonal antibodies at a high concentration 10 to 14 days later to use it as a raw material for purification of the target monoclonal antibody. As the method of purifying monoclonal antibodies, usual method for purifying immunoglobulin can be used, and it can be performed by, for example, ammonium sulfate fractionation, polyethylene fractionation, ethanol fractionation, anion exchange chromatography, affinity chromatography utilizing protein A or protein G and so forth.

<3> Production of Polyclonal Antibody that Recognizes Active HGFA and does not Substantially Recognize Inactive HGFA An active HGFA specific polyclonal antibody can be obtained by immunization with active HGFA or inactive HGFA as an antigen for immunization and purification of an antibody that recognizes active HGFA and does not substantially recognize inactive HGFA from polyclonal antibodies derived from the obtained immunized animal.

Further, as the antigen for immunization for obtaining polyclonal antibodies, the aforementioned fused substance of a peptide containing a specific antigenic site for inactive HGFA and a carrier can be used. For example, one or more kinds of substance consisting of a peptide containing any one of Sequences 1 to 25 fused to a carrier protein or a polymer compound may be mixed and used as the antigen for immunization. The animal used for the immunization is not particularly limited, and any of rabbit, goat, sheep, mouse, rat, guinea pig, fowl and so forth can be used. The antigen for immunization is sufficiently mixed with complete Freund's adjuvant, incomplete Freund's adjuvant or the like, and then inoculated to an animal subcutaneously, intramuscularly or intraperitoneally. The inoculation is performed every 2 weeks to 5 weeks and continued until antibody titer of the immunized animal with respect to the inoculated antigen sufficiently rises. Then, only the antigen is administered to the immunized animal by intravenous injection, and after 3 days to 5 days, anti-serum is collected.

As the method of purifying polyclonal antibodies from the obtained anti-serum, a usual method for purifying immunoglobulin can be used, and it can be performed by, for example, ammonium sulfate fractionation, polyethylene fractionation, ethanol fractionation, anion exchange chromatography, affinity chromatography utilizing protein A or protein G and so forth.

The purification operation for obtaining an active HGFA specific polyclonal antibody can be performed by any method so long as the method can fractionate or purify a polyclonal antibody that recognizes active HGFA and does not substantially recognize inactive HGFA, and examples of the method include, for example, ion exchange chromatography, hydrophobic chromatography, molecular sieve chromatography, reverse phase chromatography, hydroxyapatite chromatography, affinity chromatography, gel electrophoresis, immunoelectrophoresis and so forth. As one of specific methods, there can be mentioned affinity column chromatography using a resin on which active HGFA or inactive HGFA is immobilized. For example, by using the polyclonal antibodies obtained by the aforementioned method as a raw material, affinity chromatography using a resin on which inactive HGFA is immobilized is performed. By this method, polyclonal antibodies that are not bound to inactive HGFA, which exist in a non-adsorbed fraction, are collected. Then, this non-adsorbed fraction is used as a raw material to perform affinity chromatography utilizing a resin on which active HGFA is immobilized and thereby collect polyclonal antibodies that are bound to active HGFA, which exist in an adsorbed fraction.

By these methods, an active HGFA specific polyclonal antibody can be obtained. Further, for another method of the affinity chromatography, it is also possible to use a peptide containing an amino acid sequence considered to be an antigen site specific for active HGFA. For example, it is possible to utilize affinity chromatography using a resin on which one or more kinds of Sequences 1 to 25 are immobilized. For example, a resin on which a peptide containing any of Sequence 1 to 24 is immobilized can be used as an immobilization carrier for affinity chromatography used for purification of an active HGFA specific polyclonal antibody. On the other hand, a resin on which a peptide of Sequence 25 or the like is immobilized can be used as an immobilization carrier for affinity chromatography used for adsorbing or removing antibodies other than the active HGFA specific antibody.

<4> Method for Specifically Measuring Active HGFA

A method for specifically measuring active HGFA means a method comprising a process of allowing an active HGFA specific antibody to react with active HGFA. Therefore, this method is a method characterized by measuring active HGFA and not substantially measuring inactive HGFA. This method can be used for various diagnostic methods, measurement methods and assay methods, in which active HGFA in a biosample is qualitatively or quantitatively measured by using an active HGFA specific antibody of the present invention. The methods are not particularly limited so long as the methods are for a purpose of detecting active HGFA. Examples of the methods include, for example, tissue staining methods and immunoprecipitation methods for specifically detecting active HGFA, competitive binding assay methods for specifically measuring active HGFA, direct or indirect sandwich assay methods, double antibody sandwich assay methods and so forth. Further, examples of detection methods include enzyme immunoassays, radioimmunoassays, fluorescent immunoassays, chemiluminescence immunoassays, immunoblotting methods, immunochromatography methods, latex agglutination methods and so forth.

Examples of applications of immunoblotting include those utilizing active HGFA specific antibodies immobilized on a microarray or chip. It is also possible to label active HGFA specific antibodies with fluorescent label and detect its interaction with active HGFA using the fluorescence depolarization method or the fluorescence correlation variance method. It is also possible to measure the interaction of an active HGFA specific antibody with active HGFA by using a surface plasmon resonance apparatus. For example, it is possible to quantitatively measure active HGFA in a biological component by flowing a sample of the biological component containing active HGFA in a surface plasmon resonance apparatus provided with a sensor chip on which the antibodies are bonded and tracing variation of the response signal with time.

The antibody used in a method for specifically measuring active HGFA, for example, an active HGFA specific antibody, may be used as it is, or used as an antibody in the form of Fab, which is obtained by the conventional papain treatment, or in the form of F(ab')$_2$ or F(ab'), which is obtained by the pepsin treatment. Further, an antibody fragment that has a property of recognizing active HGFA and not substantially recognizing inactive HGFA also fall within the scope of the present invention. Examples of such a fragment include, for example, a fragment containing a complementation determination region (CDR) or a hypervariable region in variable domains of both of heavy chain and light chain of an active HGFA specific antibody and so forth.

The double antibody sandwich assay method for quantitatively determining active HGFA in a biological component may be, for example, a method for specifically measuring active HGFA, which comprises (1) a step of allowing a reagent comprising one or more kinds of active HGFA specific antibodies to react with active HGFA in a specimen to form an immunological reaction product, (2) a step of separating the immunological reaction product and then allowing it to react with labeled antibodies that recognize HGFA contained in the immunological reaction product, and (3) a step of measuring the labeled antibodies bound to the immunological reaction product, or a method for specifically measuring active HGFA, which comprises (1) a step of allowing a reagent comprising active HGFA and one or more kinds of active HGFA specific antibodies as primary antibodies to react with active HGFA in a specimen to form an immunological reaction product, (2) a step of separating the immunological reaction product and then allowing it to react with secondary antibodies that recognize HGFA contained in the immunological reaction product to form an immunological reaction product, (3) a step of separating the immunological reaction product and then allowing it to react with labeled antibodies that recognize the secondary antibodies contained in the immunological reaction product, and (4) a step of measuring the labeled antibodies bound to the immunological reaction product.

Specifically, active HGFA specific polyclonal antibodies or active HGFA specific monoclonal antibodies are immobilized in a conventional manner as primary antibodies on a solid phase such as microtiter wells and magnetic microbeads. Then, excessive protein bonding sites on the solid phase surface are blocked with bovine serum albumin, skim milk, gelatin or the like. Then, a biological component containing active HGFA is added to form an immunological reaction product on the solid phase and then the solid phase is washed. Subsequently, labeled polyclonal antibodies or labeled monoclonal antibodies that recognize HGFA are added as secondary antibodies and allowed to react. In this case, when monoclonal antibodies are used as the primary antibodies, labeled active HGFA specific monoclonal antibodies having an epitope different from that of the primary antibodies may be used as the secondary antibodies. Further, after washing, the amount of labeled antibodies can be measured to determine the amount of active HGFA in the biological component.

The label of the polyclonal antibodies or monoclonal antibodies used here may be an enzyme such as alkaline phosphatase, horseradish peroxidase, β-galactosidase, urease and glucose oxidase, or a fluorescent substance such as fluorescein derivatives and rhodamine derivatives. Moreover, the label may be a chemiluminescent substance such as acridinium esters or a radioactive isotope such as $^{125}$I, $^{3}$H, $^{14}$C and $^{32}$P. That is, the present invention include quantitatively determining an amount of active HGFA in a biological component using a method of measuring luminescence, fluorescence, chemiluminescence, electrochemical luminescence or radioactivity. The present invention also includes a method comprising biotinylating the secondary antibodies and detecting alkaline phosphatase, horseradish peroxidase, β-galactosidase, urease, glucose oxidase, fluorescein derivative, rhodamine derivative, a chemiluminescent substance such as acridinium esters or a radioactive isotope such as $^{125}$I, $^{3}$H, $^{14}$C and $^{32}$P forming a complex with avidin.

<5> Kit for Specifically Measuring or Staining Active HGFA

An active HGFA specific measurement kit or an active HGFA specific staining kit is a kit used for diagnosing a disease characterized by measuring or detecting active HGFA. The term "specific" used here means that, when active HGFA is measured or detected, inactive HGFA does not affect a measured value or detection value of active HGFA. It was found by the present invention for the first time that, by measuring active HGFA, diagnosis or prediction of a patient having a pathological condition, for example, a patient with organ derangement such as glomerular nephritis, nephritis, hepatitis, pancreatitis, pneumonitis, enteritis and gastritis, a cancer patient, and a patient with thrombosis such as angina pectoris, myocardial infarction and cerebral infarction. Therefore, by measuring or detecting active HGFA, various diseases such as those mentioned above can be detected. In the present invention, materials constituting the kit or methods for which the kit is used are not particularly limited so long as the kit is an active HGFA specific measurement kit for the purpose of diagnosing a disease.

Specifically, examples of the kit includes those used for diagnosing a disease by measuring or detecting active HGFA using electrophoresis, HPLC, various column chromatography techniques, various arrays and chips, surface plasmon resonance apparatus and so forth. More specifically, there can be mentioned a kit for measuring or detecting active HGFA by an immunological method utilizing an antibody. As the antibody, at least one or more kinds of the aforementioned antibodies that recognize active HGFA and do not substantially recognize inactive HGFA are used.

For example, when the kit of the present invention is based on the double antibody sandwich assay method, the kit may be a kit for specifically measuring active HGFA, which is used for a method comprising (1) a step of allowing a reagent comprising active HGFA and one or more kinds of active HGFA specific antibodies to react with active HGFA in a specimen to form an immunological reaction product, (2) a step of separating the immunological reaction product and then allowing it to react with labeled antibodies that recognize HGFA contained in the immunological reaction product, and (3) a step of measuring the labeled antibodies bound to the immunological reaction product, or a kit for specifically measuring active HGFA, which is used for a method comprising (1) a step of allowing a reagent comprising one or more kinds of active HGFA specific antibodies as primary antibodies to react with active HGFA in a specimen to form an immunological reaction product, (2) a step of separating the immunological reaction product and then allowing it to react with secondary antibodies that recognize HGFA contained in the immunological reaction product to form an immunological reaction product, (3) a step of separating the immunological reaction product and then allowing it to react with labeled antibodies that recognize the secondary antibodies contained in the immunological reaction product, and (4) a step of measuring the labeled antibodies bound to the immunological reaction product.

This kit contains at least an active HGFA specific monoclonal antibody or an active HGFA specific polyclonal antibody, and may further contain components required for the process of detecting or measuring active HGFA. Examples of the components include active HGFA or inactive HGFA as a standard protein, an enzyme, a substrate and so forth. The monoclonal antibody or polyclonal antibody contained in the kit may be an antibody labeled with an enzyme or the like, or the kit may contain a labeled antibody that recognizes the aforementioned antibody. Further, the kit may contain various buffers, solutions for diluting antigen, solutions for diluting reaction mixture, substrate solutions, solutions for stopping reaction and so forth. The kit may contain a container attached with a label and enclosing materials required for detection and quantitative determination of active HGFA. Examples of a suitable container include containers composed of glass or various plastic materials such as polypropylene, polystyrene, polycarbonate, nylon and Teflon. The kit preferably include an instruction describing a method of detecting or measuring active HGFA together with the aforementioned materials required for detecting or measuring active HGFA and a container.

<6> Active HGFA Specific Antibody Concerning Human Disease and Method for Using the Same By using the method and kit utilizing the active HGFA specific antibody according to the present invention, active HGFA in a biological component collected from a patient in a pathological condition can be detected or even quantitatively measured. The biomaterial for which active HGFA is detected is not particularly limited, and any of tissues, blood serum, plasma, urine, serous fluid, spinal fluid, extract of tissue and so forth can be used by subjecting them to a suitable pretreatment. By detecting or quantitatively determining active HGFA existing in a biomaterial collected from a patient in a pathological condition, the disease can be diagnosed and predicted or progress of the disease can be determined. Examples of the disease include organ derangement such as glomerular nephritis, nephritis, hepatitis, pancreatitis, pneumonitis, enteritis and gastritis, cancer, thrombosis such as angina pectoris, myocardial infarction and cerebral infarction and so forth.

Examples of nephritis, in particular, include mesangial proliferative nephropathy, IgA nephritis, membranoproliferative glomerulonephritis, membranous nephropathy, focal glomerular sclerosis, acute renal failure, poststreptococcal acute glomerulonephritis, chronic and acute interstitial nephritis, nephrotic syndrome and so forth. Examples of angina pectoris and myocardial infarction include stable exertional angina pectoris, unstable angina pectoris, acute myocardial infarction, old myocardial infarction and stable angina pectoris, and it is also possible to know pathological condition or prognosis of patients subjected to coronary intervention, trans-esophageal echocardiography, lower extremity artery bypass operation or aortic balloon pumping, patients with acute aortic dissection and so forth.

Moreover, since an active HGFA specific antibody can be expected to have an effect of specifically inhibiting the activity of active HGFA, it is expected to be used as a drug for therapeutic treatment of a disease caused by active HGFA. For example, active HGFA has a property of acting on inactive HGF to activate it. Therefore, an antibody that inhibits the activity of active HGFA suppresses increase of amount of active HGF emerging in living bodies, and it can be used as therapeutic or prophylactic drug for diseases considered to be caused by active HGF (WO96/38557; Genentech Incorporated, "Molecular Medicine of HGF", Medical Review, 1998), for example, cancers such as stomach cancer, lung cancer, colon cancer, spleen cancer and liver cancer as well as metastases thereof, various kinds of nephritis such as glomerular nephritis and so forth.

Existence of mouse monoclonal antibody that inhibits the activity of active HGFA (monoclonal antibody P1-4) was disclosed by Miyazawa et al. (*J. Biol. Chem.*, 271:3615–3618 (1996)), and it was elucidated by the study of the inventors of the present invention that this antibody P4-1 reacted to both of active HGFA and inactive HGFA. Since inactive HGFA abundantly exists in living bodies, it is considered that an extremely large amount of P4-1 antibodies are required for suppressing the activity of active HGFA. On the other hand, since the active type specific antibody of the present invention is presumed to be an antibody that inhibits the activity of active HGFA, it is considered that it will exert superior effect as a therapeutic drug for the aforementioned diseases with a small amount.

The antibody used for this purpose is preferably humanized by using a genetic engineering technique. Humanization of antibody can be performed by a method well known to those skilled in the art, for example, one disclosed in International Patent Publication in Japanese (Tokuhyo) No. 11-506327 and so forth.

<7> Blood Collection Method and Blood Collection Tube for Measuring Active HGFA

While the biological component for detection or measurement of active HGFA is not particularly limited, it is usually blood or a fraction or processed product thereof, and it is desirably a biological component that can be collected from a vessel such as blood, blood serum, plasma such as citrated plasma, heparin plasma and EDTA plasma, fractions or processed products thereof, or urine that can be easily collected. During collection and storage of a biological component, in particular, a manipulation for preventing inactive HGFA contained in the biological sample from being artificially converted into active HGFA is required. For example, it is desirable that collected blood serum or plasma, urine and so forth should immediately be placed under a low temperature such as under ice cooling.

Further, in order to quickly collect blood, blood serum, citrated plasma, heparin plasma or EDTA plasma from a vessel, it is desirable to use a blood collection tube. In particular, blood for use in detection or measurement of active HGFA is preferably in a state of plasma, especially citrated plasma. Further, a method of adding various protease inhibitors to the biological component for detection or measurement of active HGFA is also preferred. For example, if argatroban, which is a selective thrombin inhibitor, is added to a collected biosample in order to prevent inactive HGFA contained in a biological component from being artificially converted into active HGFA during collection or storage of the biological component, good result can be obtained. It is particularly preferable to use a tube added beforehand with argatroban for collection of blood, blood serum, citrated plasma, heparin plasma or EDTA plasma.

<8> Method for Screening of Protease Inhibitor for Active HGFA

By using an antibody that recognizes active HGFA, which does not substantially recognize inactive HGFA and does not recognize a complex of active HGFA and a protease inhibitor, a protease inhibitor that acts on active HGFA can be screened.

An antibody having the aforementioned property can be obtained by further selecting an antibody that does not recognize a complex of active HGFA and a protease inhibitor from active HGFA specific antibodies.

The aforementioned screening method specifically comprises, for example, (1) a step of mixing active HGFA and a candidate compound for protease inhibitor and allowing them to react, (2) a step of adding a monoclonal antibody that recognizes active HGFA but does not substantially recognize inactive HGFA and does not recognize a complex of active HGFA and a protease inhibitor to the mixture of active HGFA and the candidate compound for protease inhibitor, and (3) a step of separating an immnological reaction product and then measuring decrease of amount of the immunological reaction product consisting of the complex of active HGFA and the candidate compound for protease inhibitor and the antibody.

As the method of detecting the decrease of the amount of this immunological reaction product, there can be used enzyme immunoassays, radioimmunoassays, fluorescent immunoassays, chemiluminescence immunoassays, electrochemical luminescence immunoassays, immunoblotting methods, immunochromatography methods, latex agglutination methods, microarray methods that are applications of immunoblotting, and methods utilizing the fluorescence depolarization method, the fluorescence correlation variance method or a surface plasmon resonance apparatus. For example, it is possible to screen a protease inhibitor by flowing a sample of biosample in a surface plasmon resonance apparatus provided with a sensor chip on which antibodies that recognize active HGFA but do not substantially recognize inactive HGFA and do not recognize a complex of active HGFA and a protease inhibitor are bonded and tracing variation of the response signal with time.

The antibody used in this method may be used as it is, or used as an antibody in the form of Fab, which is obtained by the conventional papain treatment, or in the form of $F(ab')_2$ or $F(ab')$, which is obtained by the pepsin treatment. Further, an antibody fragment that has the property of the antibody used in this method can also be used.

BEST MODE FOR CARRYING OUT THE INVENTION

The present invention will be explained more specifically with reference to the following examples. However, the scope of the present invention is not limited to these examples.

EXAMPLE 1

Preparation of Inactive HGFA and Active HGFA

Inactive HGFA was prepared by using HGFA cDNA coding for the HGFA precursor described in Japanese Patent Laid-open Publication No. 6-153946 according to the method described in Japanese Patent Laid-open Publication No. 6-153966 to produce recombinant inactive HGFA. That is, the HGFA cDNA coding for the full length of the inactive HGFA precursor, 655 amino acids, was inserted into pcDNA3.1 (Invitrogen), which is an animal cell expression vector, downstream from a CMV promoter in a conventional manner.

The obtained expression vector was introduced into a CHO cell, which is an animal cell strain derived from a Chinese hamster ovary cell, by using a Transfectam (BioSepra) according to the attached instruction. Then, CHO cells expressing HGFA cDNA were selected by utilizing a property of a neomycin resistant gene existing on the introduced expression vector. That is, cells that could grow in an ERDF medium (Kyokuto Seiyaku) containing 400 µg/ml neomycin and 5% fetal bovine serum under 5% $CO_2$ at 37° C. were selected. Further, the selected CHO cells expressing the HGFA cDNA were cultured in an ERDF medium (Kyokuto Seiyaku) containing 100 µM nafamostat mesylate, 400 µg/ml neomycin and 5% fetal bovine serum for about 10 days to obtain about 5 L of culture supernatant.

The obtained culture supernatant was filtered, added with a protease inhibitor containing 10 mM EDTA, 10 mM benzamidine, 100 µM nafamostat mesylate, soybean trypsin inhibitor and 1000 KIU/ml aprotinin and further added with 0.5 M acetate buffer (pH 4.5) to adjust the culture supernatant to about pH 5.8. This culture supernatant was applied to a sulfated Cellofine column (Seikagaku Corporation) equilibrated with 50 mM acetate buffer (pH 5.5) containing 100 mM NaCl and washed with 50 mM acetate buffer (pH 5.5) containing 100 mM NaCl. Then, elution was performed with 50 mM sodium phosphate buffer (pH 7.5) containing 500 mM NaCl, 0.05% CHAPS (3-[(3-cholamidopropyl)dimethylammonio]propanesulfonic acid) to obtain an inactive HGFA fraction.

The obtained fraction was dialyzed against 50 mM sodium phosphate buffer (pH 7.5) containing 150 mM NaCl, applied to an A6 monoclonal antibody affinity column (Shimomura et al., *J. Biol. Chem.*, 268:22927–22932, 1993) and eluted with 50 mM glycine-HCl buffer (pH 3.0). The buffer of the obtained inactive HGFA fraction was replaced with 10 mM sodium phosphate buffer (pH 7.3) containing 100 mM NaCl and 0.05% CHAPS. A part of the fraction was added with argatroban, which is a protease inhibitor, to a final concentration of 40 µM and stored as inactive HGFA at −40° C. On the other hand, inactive HGFA not added with argatroban was added with plasma kallikrein and thrombin in an amount of 1/100 in weight ratio to the HGFA and allowed to sufficiently react at 37° C. to obtain active 36 kDa HGFA.

Further, the inactive HGFA not added with argatroban was added with thrombin in an amount of 1/100 in weight ratio to the HGFA and 10 µg/ml dextran sulfate and allowed to react at 37° C. for 20 minutes to obtain active 98 kDa HGFA. Each active HGFA fraction was purified again by using an A6 monoclonal antibody affinity column, subjected to HPLC using an Asahipak GS520HQ column (Showa Denko) equilibrated with 10 mM sodium phosphate buffer (pH 7.3) containing 100 mM NaCl and 0.05% CHAPS and stored as active 36 kDa HGFA and active 98 kDa HGFA at −40° C.

EXAMPLE 2

Preparation of ELISA Plate for Screening Active HGFA Specific Monoclonal Antibody The active 36 kDa HGFA or active 98 kDa HGFA prepared in Example 1 was diluted with hydrogenphosphate buffered physiological saline (PBS(−)) to a final concentration of 1 µg/ml as an antigen for screening hybridoma, and 100 µl of the solution was added to each well of a 96-well plate and stored at 4° C. for 24 hours so that each antigen should be adsorbed on the 96-well plate. The solution was removed from this antigen-adsorbed plate, and then 250 µl of PBS(−) containing 5% bovine serum albumin (hereafter, abbreviated as "BSA") was added to each well and left at 4° C. overnight (about 12 hours) or at 37° C. for 2 hours or longer to block the plate. Then, the plate was stored as an ELISA plate for screening active HGFA at 4° C.

Separately, the inactive HGFA prepared in Example 1 was diluted with PBS(−) to a final concentration of 1 µg/ml as an antigen for screening hybridoma. Then, 100 µl of the solution was added to each well of a 96-well plate and stored at 4° C. for 24 hours so that the antigen should be adsorbed on the 96-well plate. The solution was removed from the antigen-adsorbed plate, and then 250 µl of PBS(−) containing 5% bovine serum albumin (hereafter, abbreviated as "BSA") was added to each well and left at 4° C. overnight (about 12 hours) or at 37° C. for 2 hours or longer to block the plate. Then, the plate was stored as an ELISA plate for screening inactive HGFA at 4° C. The blocking solution in these ELISA plates was removed immediately before use.

EXAMPLE 3

Preparation of Active HGFA Specific Monoclonal Antibody

A solution containing 100 µg of the 36 kDa HGFA or 100 µg of the 98 kDa HGFA, which were prepared in Example 1, was subcutaneously and intraperitoneally administered to a Balb/c mouse with the same volume of complete Freund's adjuvant 6 times with 2-week intervals. After production of antibodies in the serum of the mouse was confirmed, a solution containing 100 µg of HGFA was administered into the caudal vein. Three days later, spleen was removed and spleen cells were fused with myeloma cells P3U1 by using polyethylene glycol 1500 according to "Monoclonal Antibody Experimental Manual" (Kodansha Scientific, 1987), introduced into wells of 96-well plate, added with HAT medium and cultured for 14 days.

Subsequently, hybridomas producing monoclonal antibodies specific to respective active HGFA in the medium were selected. That is, culture supernatant of a hybridoma subjected to selection was added to an ELISA plate for screening 36 kDa HGFA or active 98 kDa HGFA prepared in Example 2, and reactivity of the monoclonal antibodies existing in the culture supernatant was analyzed. In an amount of 100 µl/well of the culture supernatant of the hybridoma subjected to selection was added to the ELISA plate for screening each activity type and allowed to react at 4° C. for 2 hours or longer.

Then, the plate was sufficiently washed with a PBS(−) solution containing 0.05% Tween 20 (hereafter, abbreviated as "PBST solution"), and then 100 µl of PBS(−) containing 1 µg/ml HRP (horseradish peroxidase) conjugated sheep anti-mouse IgG/Fc polyclonal antibody (DAKO) and 1% BSA was added to each well and allowed to react at room temperature for 1 hour. The plate was sufficiently washed with a PBST solution, and then a citrate-phosphate buffer (pH 5.0) containing 0.4 mg/ml orthophenylenediamine (OPD, Sigma, P-9029) and a 0.015–0.03% hydrogen peroxide solution was added and allowed to react at room temperature for color development. Then, the reaction mixture was added with a 1 N $H_2SO_4$ solution to stop the reaction and measurement was performed at a measurement wavelength of 490 nm and a reference wavelength of 650 nm.

Then, by using the culture supernatant of hybridoma producing monoclonal antibodies showing reactivity to the active 36 kDa HGFA or active 98 kDa HGFA, screening was performed in the same manner on the ELISA plate for screening inactive HGFA prepared in Example 2 to select a hybridoma that does not show any reactivity to inactive HGFA. By this screening, a hybridoma producing a monoclonal antibody that recognized active 36 kDa HGFA and did not substantially recognize inactive HGFA and a monoclonal antibody that recognized active 98 kDa HGFA and did not recognize inactive HGFA (AHGA-A, AHGA-B, AHGA-C) were obtained. Each obtained hybridoma was subjected to four times of cloning operations by a limited dilution method, and its culture supernatant was collected and subjected to affinity chromatography utilizing protein A (Amersham Pharmacia Biotec) to purify monoclonal antibodies.

The hyboridoma clone AHGA-A was deposited since Oct. 19, 2001 in National Institute of Advanced Industrial Science and Technology, International Patent Organism Depositary (Tsukuba Central 6, 1-1, Higashi 1-Chome, Tsukuba-shi, Ibaraki-ken, 305–8566, Japan) as deposition number of FERM BP-7779.

EXAMPLE 4

Analysis of Reaction Specificity of Active HGFA Specific Monoclonal Antibody

Among active HGFA specific monoclonal antibodies prepared and purified in Example 3, reactivities of monoclonal antibodies derived from hybridoma clones AHGA-A, AHGA-B and AHGA-C were analyzed. To this purpose, 100 µl of PBS(−) containing about 1 µg/ml monoclonal antibodies derived from each of hybridoma clones AHGA-A, AHGA-B and AHGA-C and 1% BSA was added to each well of the ELISA plate for screening active 36 kDa HGFA or active 98 kDa HGFA or ELISA plate for screening inactive HGFA prepared in Example 2 and allowed to react at 4° C. for 2 hours or longer.

Subsequently, the plate was sufficiently washed with a PBS(−) solution containing 0.05% Tween 20 (hereafter, abbreviated as "PBST solution"), and then 100 µl of PBS(−) containing 1 µg/ml HRP-conjugated sheep anti-mouse IgG polyclonal antibody (DAKO) and 1% BSA was added to each well and further allowed to react at room temperature for 1 hour. The plate was sufficiently washed with a PBST solution, and then a citrate-phosphate buffer (pH 5.0) containing 0.4 mg/ml orthophenylenediamine (OPD, Sigma, P-9029) and a 0.015–0.03% hydrogen peroxide solution was added and allowed to react at room temperature for color development.

Then, the reaction mixture was added with a 1 N $H_2SO_4$ solution to stop the reaction and measurement was performed at a measurement wavelength of 490 nm and a reference wavelength of 650 nm. The measurement results are shown in FIG. 1. The monoclonal antibodies derived from hybridoma clones AHGA-A and AHGA-B were reactive to active 36 kDa HGFA, but not reactive to inactive HGFA. Further, those of the hybridoma clone AHGA-C was reactive to active 98 kDa HGFA, but not reactive to inactive HGFA (FIG. 1). Separately, reactivities to active 36 kDa HGFA and inactive HGFA of existing monoclonal antibodies directed to HGFA (7E10, P1-4, A-1, A-6, A-23, A-32, A-51, A-75) were analyzed. As a result, they showed equivalent reactivities to both the active HGFA and inactive HGFA and did not have a reactivity specific to active HGFA unlike the monoclonal antibodies obtained in the present invention.

EXAMPLE 5

Measurement of Dissociation Constant of Active HGFA Specific Monoclonal Antibody Among active HGFA specific monoclonal antibodies prepared and purified in the Example 3, the dissociation constant was measured for the monoclonal antibody derived from the hybridoma clone AHGA-A. An active HGFA immobilized plate on which active HGFA was immobilized and blocked with BSA was added with the antibodies at different antibody concentrations and allowed to sufficiently react until equilibrium was reached (2 hours or longer).

Subsequently, the plate was sufficiently washed with a PBS(−) solution containing 0.05% Tween 20 (hereafter, abbreviated as "PBST solution"), and then 100 µl of PBS(−) containing 1 µg/ml of HRP (horseradish peroxidase) conjugated goat anti-mouse IgG/Fc polyclonal antibody (ICN) and 1% BSA was added to each well and further allowed to react at room temperature for 1 hour. The plate was sufficiently washed with a PBST solution, and then a citrate-phosphate buffer (pH 5.0) containing 0.4 mg/ml orthophenylenediamine (OPD, Sigma, P-9029) and a 0.015–0.03% hydrogen peroxide solution were added and allowed to react at room temperature for color development.

Then, the reaction mixture was added with a 1 N $H_2SO_4$ solution to stop the reaction and measurement was performed at a measurement wavelength of 490 nm and a reference wavelength of 650 nm. A dissociation constant was obtained from the measurement result by Schatchard plot. As a result, it was $4.05 \times 10^{-10}$ M. This result suggests that the antibody of the present invention has high affinity.

EXAMPLE 6

Preparation of Monoclonal Antibody that Specifically Recognizes Active HGFA and does not Recognize Complex of Active HGFA and Protease Inhibitor The hybridomas producing a monoclonal antibody that specifically recognized active HGFA and did not recognize inactive HGFA selected in Example 3 were further screened as follows.

The blocking solution was removed from the plate for screening active 36 kDa HGFA or active 98 kDa HGFA prepared in Example 2, and then 20 µl of PBS(−) containing 200 µM nafamostat mesylate, which is a protease inhibitor, was added to each well and allowed to react at room temperature for 1 hour to form a complex of active HGFA and nafamostat mesylate. Then, 100 µl of the culture supernatant of the hybridoma subjected to selection was added to each well and allowed to react at 4° C. for 2 hours.

Subsequently, the plate was sufficiently washed with a PBS(−) solution containing 0.05% Tween 20 (hereafter, abbreviated as "PBST solution"), and then 100 µl of PBS(−) containing 1 µg/ml HRP-conjugated sheep anti-mouse IgG polyclonal antibody (DAKO) and 1% BSA was added to each well and further allowed to react at room temperature for 1 hour. The plate was sufficiently washed with a PBST solution, and then a citrate-phosphate buffer (pH 5.0) containing 0.4 mg/ml orthophenylenediamine (OPD, Sigma, P-9029) and a 0.015–0.03% hydrogen peroxide solution was added and allowed to react at room temperature for color development.

Then, the reaction mixture was added with a 1 N $H_2SO_4$ solution to stop the reaction and measurement was performed at a measurement wavelength of 490 nm and a reference wavelength of 650 nm. By this screening, a monoclonal antibody that did not recognize a complex of active 36 kDa HGFA and nafamostat mesylate was selected. A hybricoma clone producing the selected monoclonal antibody was designated as AHGA-D. Each of the obtained hybridomas was subjected to 4 times of cloning operations by a limited dilution method, and then its culture supernatant was collected and subjected to affinity chromatography utilizing protein A to purify the monoclonal antibody.

EXAMPLE 7

Analysis of Reaction Specificity of Monoclonal Antibody that Specifically Recognizes Active HGFA and does not Recognize Complex of Active HGFA and Protease Inhibitor The reactivity of the monoclonal antibody derived from the hybridoma clone AHGA-D selected in Example 6 was analyzed. In an amount of 20 µl of PBS(−) containing nafamostat mesylate was added at a concentration of 0, 0.820, 7.40, 22.20 or 2000 µM to each well of the ELISA plate for screening active 36 kDa HGFA prepared in Example 2 and allowed to react at room temperature for 1 hour to form a complex of active HGFA and nafamostat mesylate. Then, 100 μl of PBS(−) containing about 1 μg/ml the monoclonal antibody derived from the hybridoma clone AHGA-D, 1% BSA and nafamostat mesylate at various concentrations (0, 0.820, 7.40, 22.20 and 2000 μM) was added to each well and allowed to react at 4° C. for 2 hours or longer.

Subsequently, the plate was sufficiently washed with a PBS(−) solution containing 0.05% Tween 20 (hereafter, abbreviated as "PBST solution"), and then 100 μl of PBS(−) containing 1 μg/ml HRP-conjugated sheep anti-mouse IgG polyclonal antibody (DAKO) and 1% BSA was added to each well and further allowed to react at room temperature for 1 hour. The plate was sufficiently washed with a PBST solution, an then a citrate-phosphate buffer (pH 5.0) containing 0.4 mg/ml orthophenylenediamine (OPD, Sigma, P-9029) and a 0.015–0.03% hydrogen peroxide solution was added and allowed to react at room temperature for color development.

Figure 2:
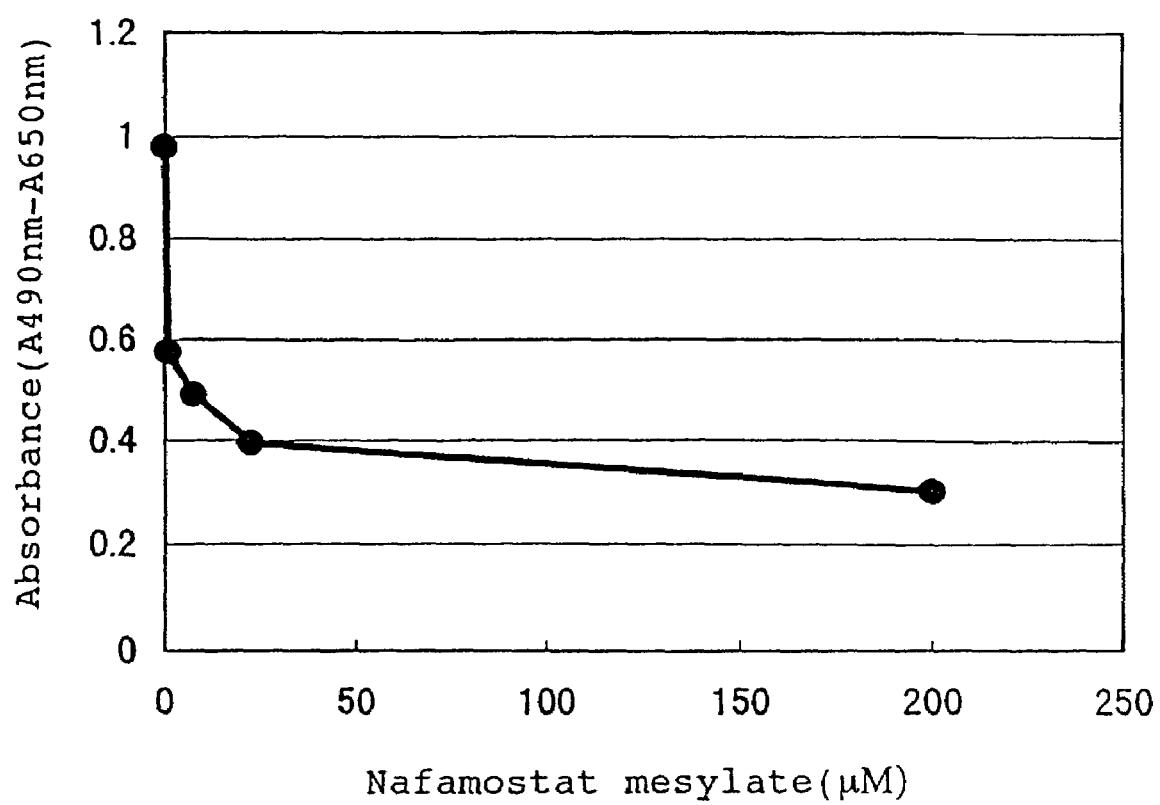
FIG. 2 shows reactivity between a complex of active HGFA and protease inhibitor and a monoclonal antibody.

Then, the reaction mixture was added with a 1 N $H_2SO_4$ solution to stop the reaction and measurement was performed at a measurement wavelength of 490 nm and a reference wavelength of 650 nm. The measurement results are shown in FIG. 2. The reactivity of the monoclonal antibody derived from the hybridoma clone AHGA-D to HGFA bonded to nafamostat mesylate, which is a protease inhibitor, was markedly lowered.

EXAMPLE 8

Preparation of Polyclonal Antibody Directed to HGFA and Labeled Version thereof

Polyclonal antibodies directed to HGFA were prepared by subcutaneously administering a mixture of 100 μg each of active 36 kDa HGFA, active 98 kDa HGFA and inactive HGFA prepared in Example 1 to a rabbit 7 times with 2-week intervals. After production of antibodies in the serum was confirmed, 10 μg each of the antigen was further intravenously administered and the antiserum was obtained 5 days later. Further, after precipitation with ammonium sulfate, anti-HGFA polyclonal antibodies were obtained by purification using protein A column. Then, the obtained HGFA polyclonal antibodies were labeled with biotin to prepare biotin-labeled anti-HGFA polyclonal antibodies.

EXAMPLE 9

Construction of Active HGFA Specific Measurement System

The monoclonal antibody derived from the hybridoma clone AHGA-A used in Example 4 was used as a primary antibody. This monoclonal antibody was dissolved in 0.05 M carbonate-bicarbonate buffer (pH 9.6) at a concentration of 30 μg/ml, added to a 96-well plate in an amount of 100 μl/well and left at 4° C. for one day (about 12 hours or longer). The primary antibody solution was removed from this primary antibody-coated plate, and then 250–300 μl/well of PBS(−) containing 1% BSA was added and left at 4° C. overnight (about 12 hours) or at 37° C. for 2 hours or longer. The blocking solution was removed from this plate, and then active 36 kDa HGFA or inactive 98 kDa HGFA dissolved in 100 μl of 0.15 M NaCl, 0.1% CHAPS, 0.05% Tween 20, 0.05% Az (sodium azide), 0.1% BSA, 20 mM sodium phosphate buffer (pH 7.5) was added at various concentrations (0, 0.69, 2.1, 6.2, 18.5, 55.6, 167 and 500 ng/ml) and allowed to react at 4° C. for about 2 hours or longer.

Subsequently, the plate was sufficiently washed by using a washing solution containing 500 mM NaCl, 0.05% Tween 20 and 20 mM Tris-HCl (pH 7.5), and then 100 μl of PBS(−) containing 1 μg/ml biotin-labeled anti-HGFA polyclonal antibody prepared in Example 8 and 1% BSA was added to each well and allowed to react in an incubator at 37° C. for 2 hours.

Then, the plate was sufficiently washed by using the above washing solution, and then 100 μl of PBS(−) containing 1% BSA in which HRP-conjugated streptavidin (Amersham Pharmacia Biotech, Code RPN1231) was diluted at a ratio of 1:2000 was added to each well and further allowed to react at room temperature for 1 hour. The plate was sufficiently washed with a washing solution, and then 100 μl/well of a citric acid-phosphate buffer containing 0.4 mg/ml orthophenylenediamine (OPD, Sigma, P-9029) and 0.015–0.03% hydrogen peroxide solution (pH 5.0) was added and allowed to react at room temperature for color development.

Figure 3A:
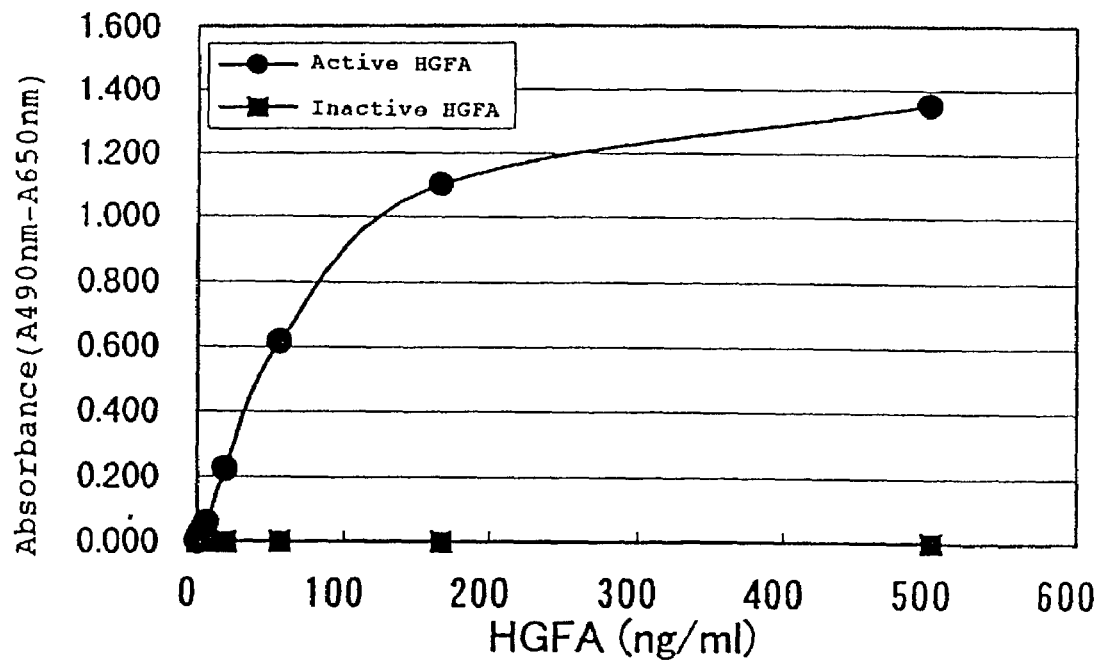
FIG. 3A shows the concentration of HGFA in the range of 0–500 ng/ml.
Figure 3B:
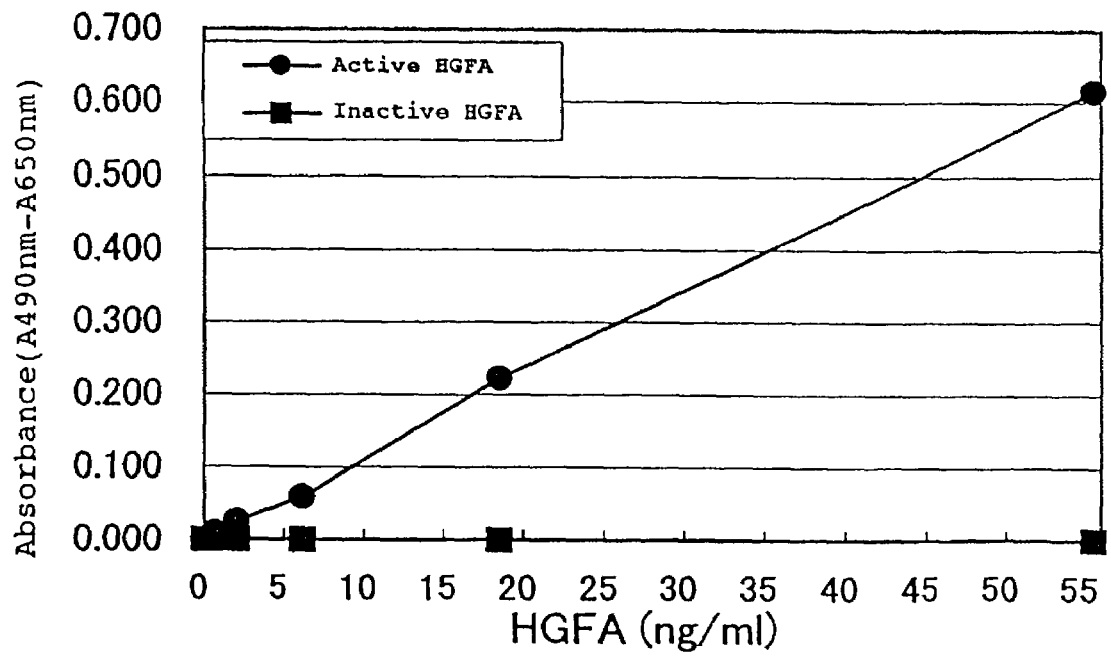
In FIG. 3B, the HGFA concentration range of 0–55.6 ng/ml shown in FIG. 3A is enlarged.

Subsequently, the reaction mixture was added with 100 μl/well of 1 N $H_2SO_4$ solution to stop the reaction and measurement was performed at a measurement wavelength of 490 nm and a reference wavelength of 650 nm. The results are shown in FIG. 3. FIG. 3A shows the concentration of HGFA in the range of 0–500 ng/ml. In FIG. 3B, the concentration range of 0–55.6 ng/ml shown in FIG. 3A is enlarged.

EXAMPLE 10

Measurement of Active HGFA Amount in Blood of Healthy Subject

Sera of 144 healthy subjects were used for the measurement utilizing the active HGFA specific measurement system prepared in Example 9. Each serum of healthy subject was collected, frozen, stored and thawed immediately before use in this experiment. First, on the 96-well plate coated with the primary antibody and blocked prepared in Example 9, 50 μl of 0.15 M NaCl, 0.1% CHAPS, 0.05% Tween 20, 0.05% Az, 0.1% BSA, 20 mM sodium phosphate buffer (pH 7.5) was added to each well in advance, and 50 μl of a serum of healthy subject or standard 36 kDa active HGFA (0, 0.69, 2.1, 6.2, 18.5, 55.6, 167 or 500 ng/ml) was added to each well and allowed to react at 4° C. for about 2 hours or longer. Then, the plate was washed by using a washing solution containing 500 mM NaCl, 0.05% Tween 20 and 20 mM Tris-HCl (pH 7.5), and then 100 μl of PBS(−) containing 1 μg/ml biotin-labeled anti-HGFA polyclonal antibody prepared in Example 8 and 1% BSA was added to each well and allowed to react in an incubator at 37° C. for 2 hours. Subsequently, the plate was sufficiently washed by using the above washing solution, and 100 μl of PBS(−) containing 1% BSA in which HRP-conjugated streptavidin (Amersham Pharmacia Biotec, Code RPN1231) was diluted at a ratio of 1:2000 was added to each well and further allowed to react at room temperature for 1 hour.

Figure 4:
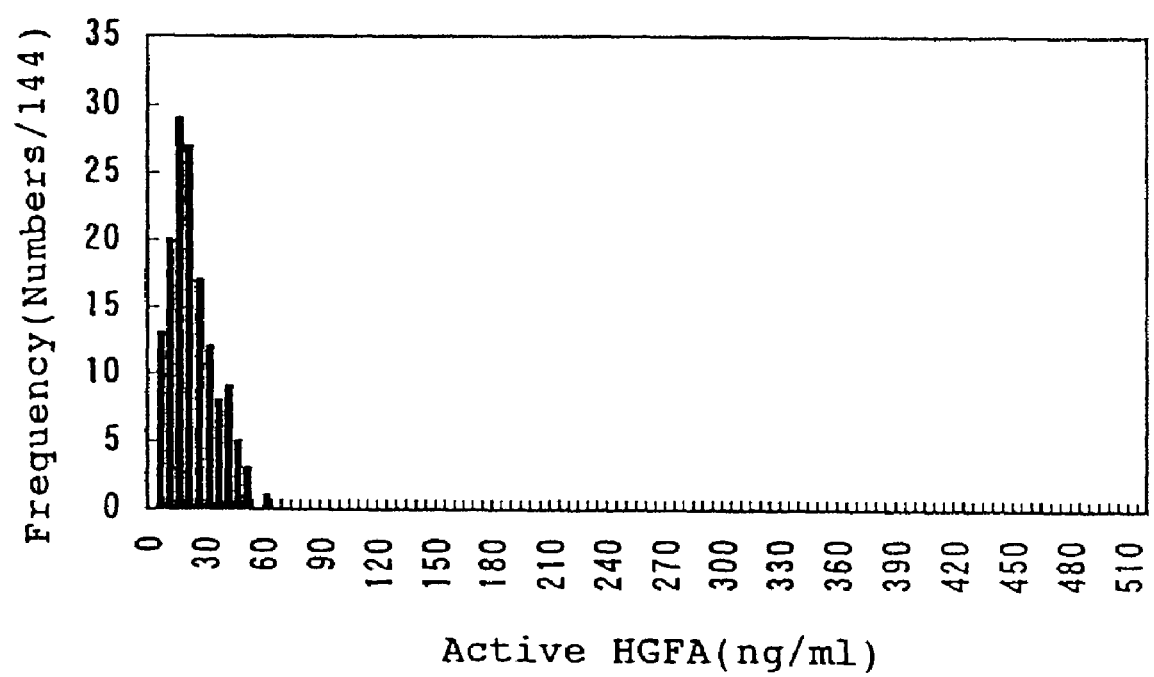
FIG. 4 shows a histogram of amounts of active HGFA in sera of healthy subjects.

The plate was sufficiently washed with a washing solution, and then 100 μl/well of a citric acid-phosphate buffer containing 0.4 mg/ml orthophenylenediamine (OPD, Sigma, P-9029) and a 0.015–0.03% hydrogen peroxide solution (pH 5.0) was added and allowed to react at room temperature for color development. Then, 100 μl/well of 1 N $H_2SO_4$ solution was added to stop the reaction and measurement was performed at a measurement wavelength of 490 nm and a reference wavelength of 650 nm. Then, a calibration curve was drawn based on the relationship between the standard 36 kDa active HGFA concentration and the color development amount to calculate the concentration in each serum of healthy subject. The results are shown in FIG. 4. The concentration in the sera of normal subjects was in the range of 0 to 58.5 ng/ml and the average was 19 ng/ml.

EXAMPLE 11

Measurement of Active HGFA Level in Blood of Patients with Various Human Diseases Sera of patients with various human diseases were used for measurement performed according to the method of Example 10 by using the active HGFA specific measurement system prepared in Example 9. The number of patients for each disease was 5. Each serum was collected, frozen, stored and thawed immediately before use in the experiment. The results are shown in Table 1. It was found that the concentration of active HGFA was higher in blood of patients with glomerular nephritis, pancreatitis, cancer, myocardial infarction, angina pectoris and cerebral infarction, compared with that of healthy subjects (number of specimen: 9, average value:

TABLE 1

| Case | Patient 1 | Patient 2 | Patient 3 | Patient 4 | Patient 5 |
|---|---|---|---|---|---|
| Glomerular nephritis | 304.2 | 158.3 | 130.0 | 144.8 | 280.7 |
| Pancreatitis | 108.1 | 100.0 | 152.0 | 109.6 | 117.6 |
| Cancer | 104.1 | 153.9 | 141.6 | 80.9 | 105.4 |
| Myocardial infarction | 61.6 | 69.2 | 240.7 | 70.1 | — |
| Angina pectoris | 175.5 | 134.0 | 270.7 | 213.8 | 374.3 |
| Cerebral infarction | 64.8 | 96.2 | 554.0 | — | — |

EXAMPLE 12

Figure 5:
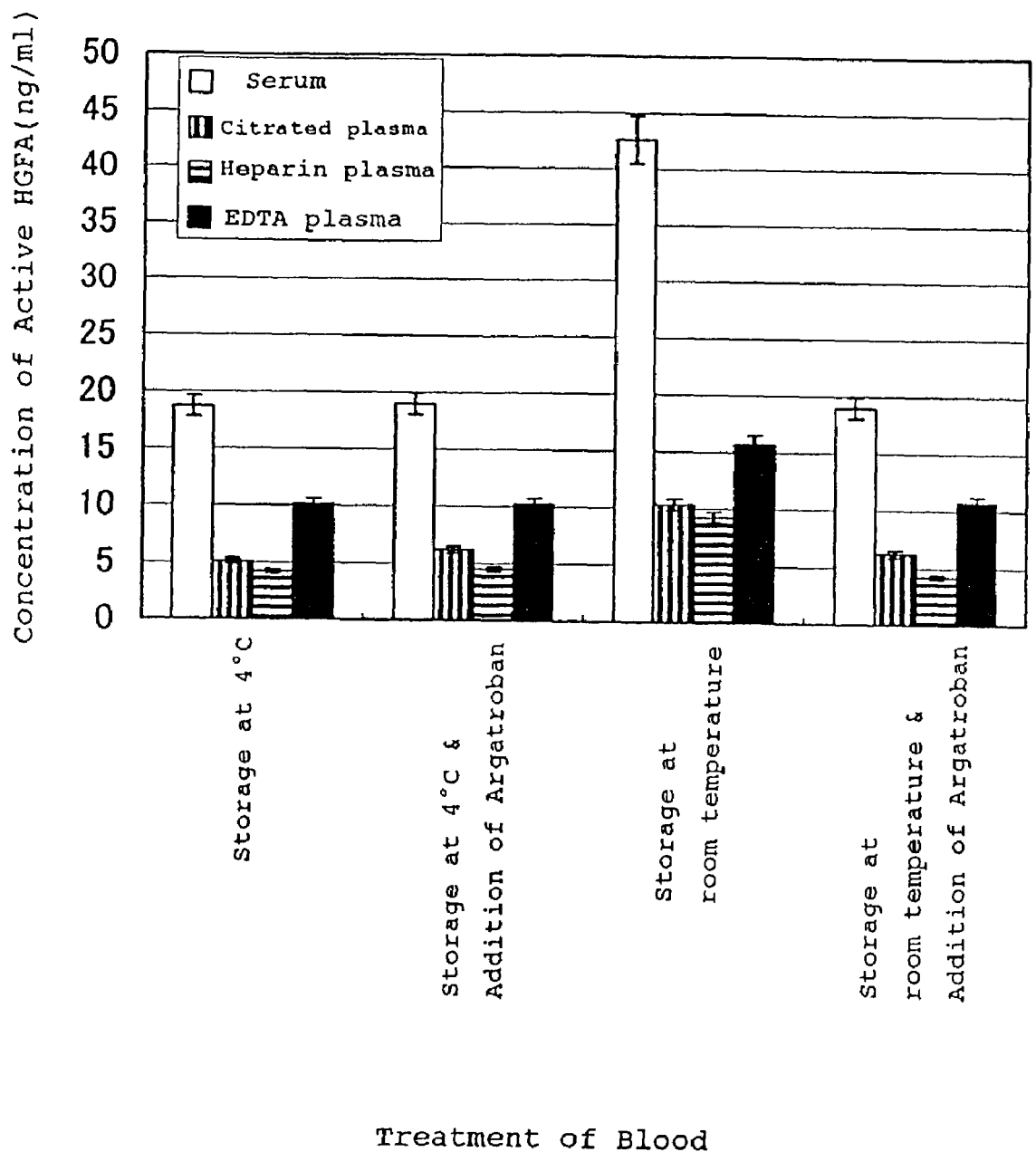
FIG. 5 shows storage stability of active HGFA value in serum, citrated plasma, heparin plasma and EDTA plasma, and effect of addition of argatroban.

Method for Collecting Blood for Measuring Active HGFA and Examination of Stability Serum, citrated plasma, heparin plasma or EDTA plasma was collected from a normal subject or serum, and citrated plasma, heparin plasma or EDTA plasma containing argatroban at a final concentration of 40 μM was prepared. Each was stored at 4° C. or 37° C. for 12 hours. Then, the amount of active HGFA was measured by the method described in Example 10. The results are shown in FIG. 5. It was found that the increase in the amount of active HGFA due to storage of serum or plasma was less in plasma than in serum and that this increase was favorably suppressed by addition of argatroban.

The application is based on Japanese patent application No. 2000-370435 which was filed in Japan on Dec. 5, 2000 is incorporated by reference herein in its entirety.

What is claimed is:

1. An antibody that recognizes an active hepatocyte growth factor activator (HGFA) activated by limited proteolysis of inactive HGFA, which is a precursor of active HGFA, between arginine at a position of 407 and isoleucine at a position of 408 which correspond to amino acid positions 13 and 14 of SEQ ID NO: 3 as counted from a translation initiation amino acid of inactive HGFA, and has a dissociation constant of $1\times10^{-5}$ M or higher for inactive HGFA, and a dissociation constant of $1\times10^{-5}$ M or lower for active HGFA.

2. The antibody according to claim 1, which has a dissociation constant of $1\times10^{-9}$ M or lower for active HGFA.

3. The antibody according to claim 1 or 2, which is a monoclonal antibody.

4. The antibody according to claim 3, which recognizes active HGFA having a molecular weight of about 34,000–98,000 determined by the SDS-PAGE method.

5. The antibody according to claim 4, which recognizes active HGFA having a molecular weight of about 34,000–38,000 determined by the SDS-PAGE method.

6. The antibody according to claim 4, which is produced by a hybridoma of an accession number FERM BP-7779.

7. A momoclonal antibody that recognizes active HGFA activated by limited proteolysis of inactive HGFA, which is a precursor of active HGFA, between arginine at a position of 407 and isoleucine at a position of 408 which correspond to amino acid positions 13 and 14 of SEQ ID NO: 3 as counted from a translation initiation amino acid of inactive HGFA, and has a dissociation constant of $1\times10^{-5}$ M or higher for inactive HGFA and a dissociation constant of $1\times10^{-8}$ M or lower for active HGFA.

8. The monoclonal antibody according to claim 7, which has a dissociation constant of $1\times10^{-9}$ M or lower for active HGFA.

9. A hybridoma cell line that produces a monoclonal antibody according to claim 3.

10. A hybridoma cell line that produces a monoclonal antibody according to claim 7.

11. A hybridoma cell line that produces the monoclonal antibody according to claim 8.

12. A kit for detecting or measuring active HGFA, which comprises one or more antibodies that recognize an active HGFA activated by limited proteolysis of inactive HGFA, which is a precursor of active HGFA, between arginine at a position of 407 and isoleucine at a position of 408 which correspond to amino acid positions 13 and 14 of SEQ ID NO: 3 as counted from a translation initiation amino acid of inactive HGFA, and has a dissociation of $1\times10^{-5}$ M or higher for inactive HGFA and a dissociation constant of $1\times10^{-8}$ M or lower for active HGFA.

13. The kit according to claim 12, wherein the one or more antibodies has a dissociation constant of $1\times10^{-9}$ M or lower for active HGFA.

14. The kit according to claim 12, wherein the kit further comprises an active HGFA activated by limited proteolysis of inactive HGFA, which is a precursor of active HGFA, between arginine at a position of 407 and isoleucine at a position of 408 which correspond to amino acid positions 13 and 14 of SEQ ID NO: 3 as counted from a translation initiation amino acid of inactive HGFA.

15. The kit according to any one of claims 12 to 14, which is used for the diagnosis of disease selected from the group consisting of organ inflammation, glomerular nepbritis, cancer, myocardial infarction, angina pectoris, cerebral infarction or thrombosis.

16. The kit according to any one of claims 12 to 14, which is used to measure active HGFA in a biological component collected from a subject suspected of having a disease.

17. The kit according to any one of claims 12 to 14, wherein the active HGFA is detected or measured by immunostaining.

18. A method for producing an antibody tat recognizes an active HGFA and has a dissociation constant of $1\times10^{-5}$ M or higher for an inactive HGFA and a dissociation constant of $1\times10^{-8}$ M or lower for an active HGFA, comprising the steps of:

(i) immunizing a mouse with an active HGFA as an antigen to produce antibody-producing cells in the spleen or lymph node of said immunized mouse, (ii) collecting antibody-producing cells from the spleen or lymph node of said immunized mouse;

(iii) fusing the antibody-producing cells with rat myeloma cells to produce hybridomas, (iv) selecting hybridomas producing the antibody that recognizes an active HGFA activated by limited proteolysis of inactive HGFA, which is a precursor of active HGFA, between arginine at a position of 407 and isoleucine at a position of 408 which correspond to amino acid positions 13 and 14 of SEQ ID NO: 3 as counted from a translation initiation amino acid of inactive HGFA, and has a dissociation constant of $1\times10^{-5}$ M or higher for an inactive HGFA and a dissociation constant of $1\times10^{-8}$ M or lower for an active HGFA, and (v) culturing the selected hybridomas in a medium and collecting the antibody from the supernatant of the medium.

* * * * *

UNITED STATES PATENT AND TRADEMARK OFFICE
CERTIFICATE OF CORRECTION

PATENT NO.         : 7,045,602 B2
APPLICATION NO. : 10/000096
DATED                  : May 16, 2006
INVENTOR(S)       : Daiji Naka et al.

It is certified that error appears in the above-identified patent and that said Letters Patent is hereby corrected as shown below:

In column 6, line 23, please delete "Pat. No." after "U.S." before "5,466,593".

In column 6, line 24, please delete "Pat. No." after "U.S." before "5,677,164".

In column 9, line 20, please replace "Sequence GRRHKKRTFLRPRIIGGSSSLPGSHP (SEQ. ID. NO.: 3) 25:" with --Sequence 25: GRRHKKRTFLRPRIIGGSSSLPGSHP (SEQ. ID. NO.: 3)--.

In column 10, line 48, please replace "37° C." with --37° C --.

In column 10, line 49, please replace "30° C. to 37° C." with --30° C to 37° C --.

In column 18, line 57, please replace "37° C." with --37° C--.

In column 19, line 23, please replace "37° C." with --37° C--.

In column 19, line 28, please replace "37° C." with --37° C--.

In column 19, line 47, please replace "4° C." with --4° C--.

In column 19, line 51, please replace "4° C." with --4° C--.

In column 19, line 52, please replace "37° C." with --37° C--.

In column 19, line 59, please replace "4° C." with --4° C--.

In column 19, line 63, please replace "4° C." with --4° C--.

In column 19, line 64, please replace "37° C." with --37° C--.

In column 20, line 28, please replace "4° C." with --4° C--.

In column 21, line 15, please replace "4° C." with --4° C--.

In column 22, line 29, please replace "4° C." with --4° C--.

In column 23, line 5, please replace "4° C." with --4° C--.

UNITED STATES PATENT AND TRADEMARK OFFICE
CERTIFICATE OF CORRECTION

PATENT NO. : 7,045,602 B2
APPLICATION NO. : 10/000096
DATED : May 16, 2006
INVENTOR(S) : Daiji Naka et al.

It is certified that error appears in the above-identified patent and that said Letters Patent is hereby corrected as shown below:

In column 23, line 55, please replace "4° C." with --4° C--.

In column 23, line 59, please replace "4° C." with --4° C--.

In column 23, line 59, please replace "37° C." with --37° C--.

In column 23, line 66, please replace "4° C." with --4° C--.

In column 24, line 6, please replace "37° C." with --37° C--.

In column 24, line 45, please replace "4° C." with --4° C--.

In column 24, line 51, please replace "37° C." with --37° C--.

In column 25, line 25, please add --19 ng/ml).-- after "9, average value:".

In column 26, line 25, please replace "4° C." with --4° C--.

In column 26, line 25, please replace "37° C." with --37° C--.

Claim 1

In column 27, line 20, please replace "of 1 x $10^{-5}$ M or lower" with --of 1 x $10^{-8}$ M or lower--.

Claim 15

In column 28, line 24, please replace "glomerular nepbritis" with --glomerular nephritis--.

UNITED STATES PATENT AND TRADEMARK OFFICE
CERTIFICATE OF CORRECTION

PATENT NO. : 7,045,602 B2
APPLICATION NO. : 10/000096
DATED : May 16, 2006
INVENTOR(S) : Daiji Naka et al.

It is certified that error appears in the above-identified patent and that said Letters Patent is hereby corrected as shown below:

<u>Claim 18</u>

In column 28, line 34, please replace "tat recognizes" with --that recognizes--.

Signed and Sealed this

Twenty-first Day of November, 2006

JON W. DUDAS
*Director of the United States Patent and Trademark Office*